(12) United States Patent
Rettaliata

(10) Patent No.: US 10,076,629 B1
(45) Date of Patent: Sep. 18, 2018

(54) DEVICE FOR DIRECTING NEBULIZED VAPOR

(71) Applicant: Justin Michael Rettaliata, Arlington, VA (US)

(72) Inventor: Justin Michael Rettaliata, Arlington, VA (US)

( * ) Notice: Subject to any disclaimer, the term of this patent is extended or adjusted under 35 U.S.C. 154(b) by 397 days.

(21) Appl. No.: 14/705,027

(22) Filed: May 6, 2015

Related U.S. Application Data

(60) Provisional application No. 62/119,306, filed on Feb. 23, 2015.

(51) Int. Cl.
| | | |
|---|---|---|
| A61M 15/00 | (2006.01) |
| A61M 11/06 | (2006.01) |
| A61M 16/14 | (2006.01) |
| A61M 11/00 | (2006.01) |

(52) U.S. Cl.
CPC ............ *A61M 16/14* (2013.01); *A61M 11/00* (2013.01); *A61M 11/06* (2013.01); *A61M 15/00* (2013.01); *A61M 2205/59* (2013.01); *A61M 2240/00* (2013.01)

(58) Field of Classification Search
CPC ....... A61M 11/00–11/08; A61M 15/00; A61M 15/0085; A61M 15/0086–15/0088; A61M 16/14; A61M 2205/59; A61M 2240/00
See application file for complete search history.

(56) References Cited

U.S. PATENT DOCUMENTS

| | | | | |
|---|---|---|---|---|
| 5,312,281 | A * | 5/1994 | Takahashi | A63H 17/34 239/102.2 |
| 5,685,291 | A * | 11/1997 | Marsh | A61M 15/0086 128/200.15 |
| 5,690,096 | A * | 11/1997 | Burch | A61M 16/06 128/200.24 |
| 5,704,344 | A * | 1/1998 | Cole | A61M 15/00 128/200.14 |
| 5,853,002 | A * | 12/1998 | Kawasaki | A61M 11/06 128/200.14 |
| 6,578,571 | B1 * | 6/2003 | Watt | A61M 15/00 128/200.14 |
| 7,350,520 | B1 * | 4/2008 | Richard-Bey | A61M 11/06 128/200.14 |

* cited by examiner

*Primary Examiner* — Valerie L Woodward

(57) ABSTRACT

A device for directing a nebulized mixture includes a receiver, disposed at lower end of the device, to receive a nebulizer, an exhaust port to expel a nebulized mixture from the device, and a passage to transport the nebulized mixture from the nebulizer to the exhaust port. The device has an external shape of a novelty.

10 Claims, 38 Drawing Sheets

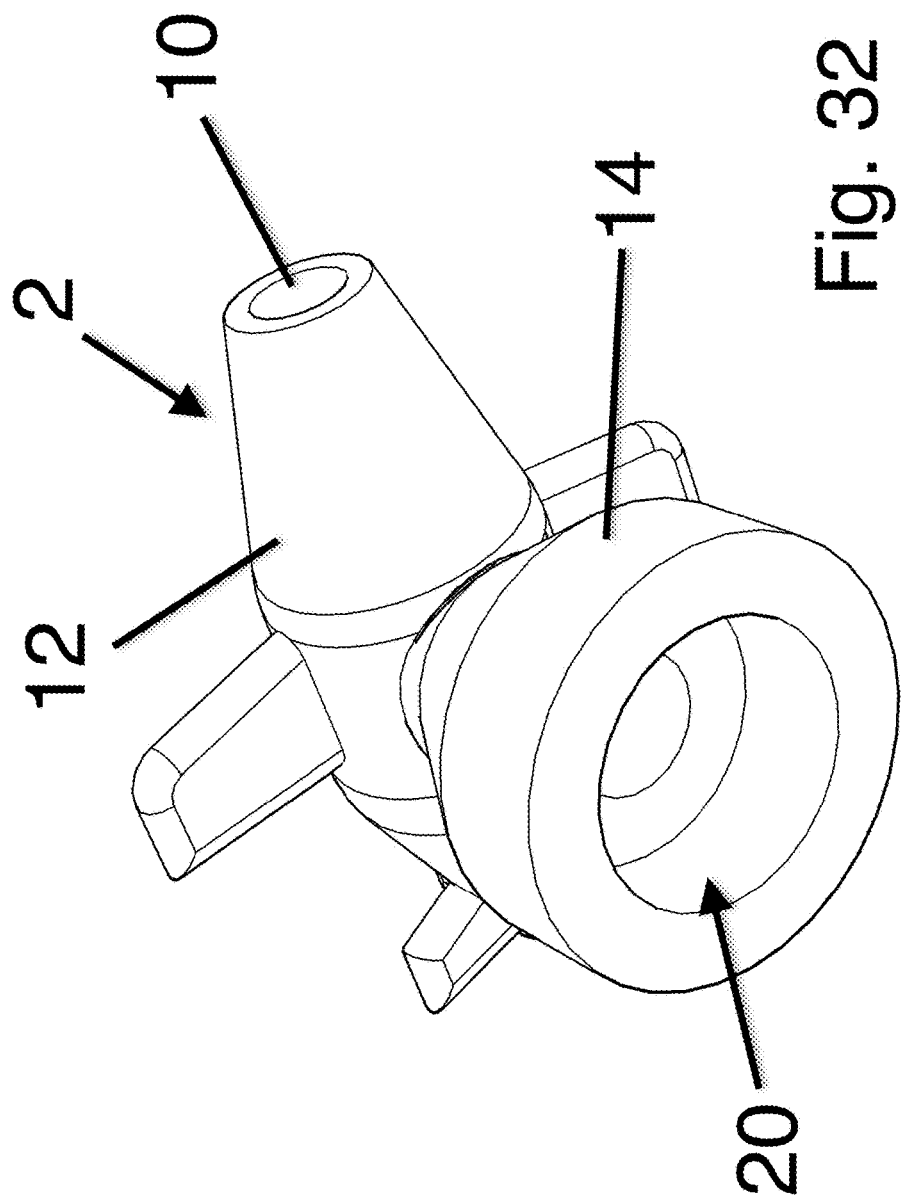

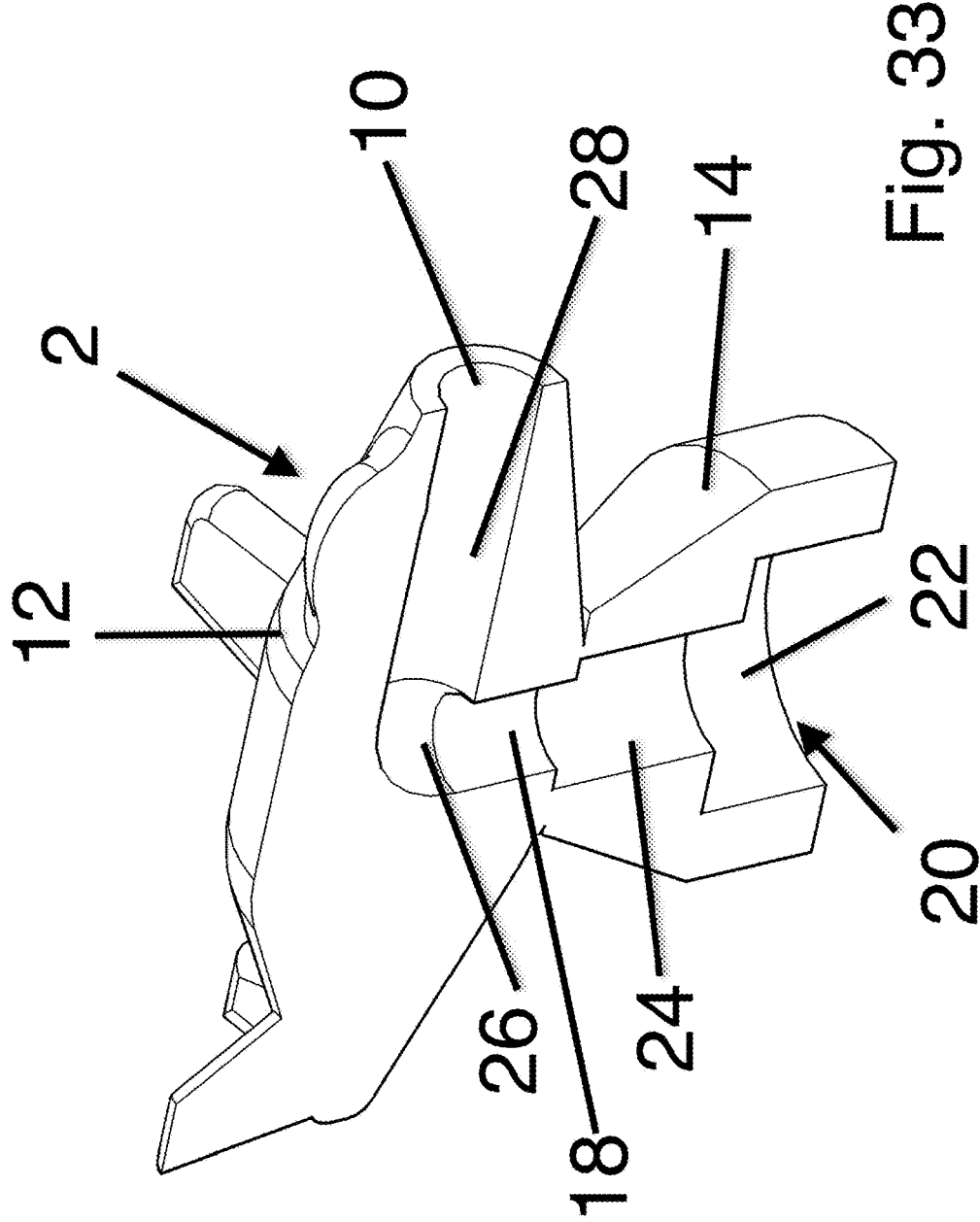

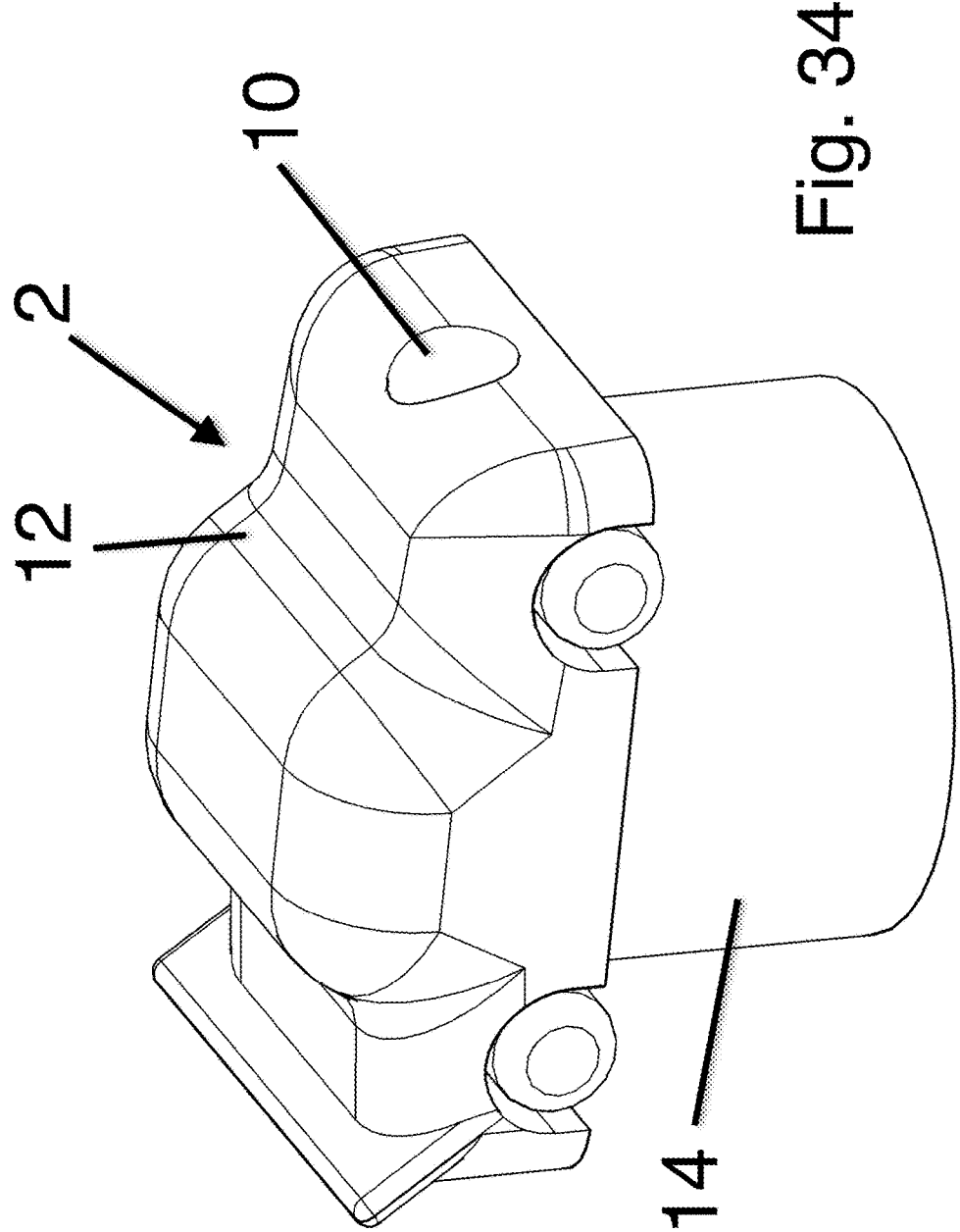

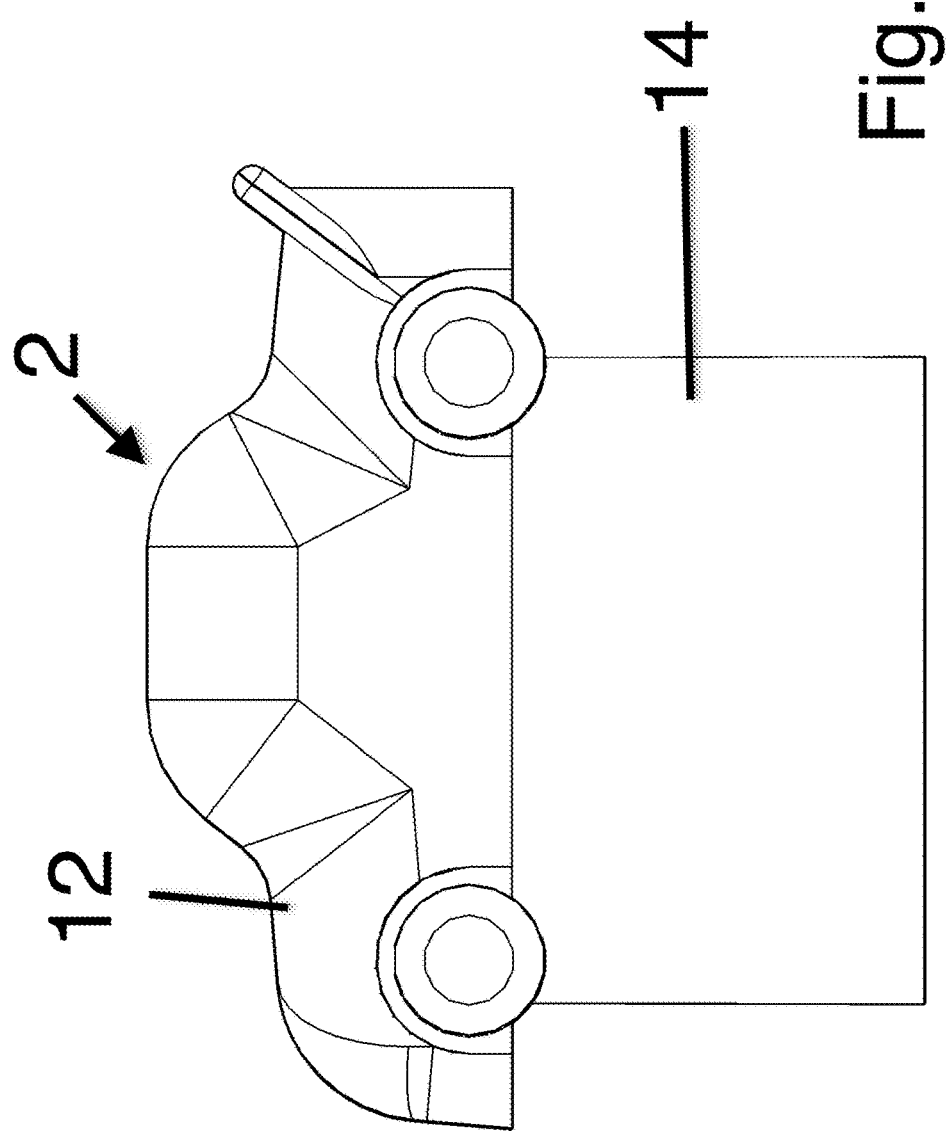

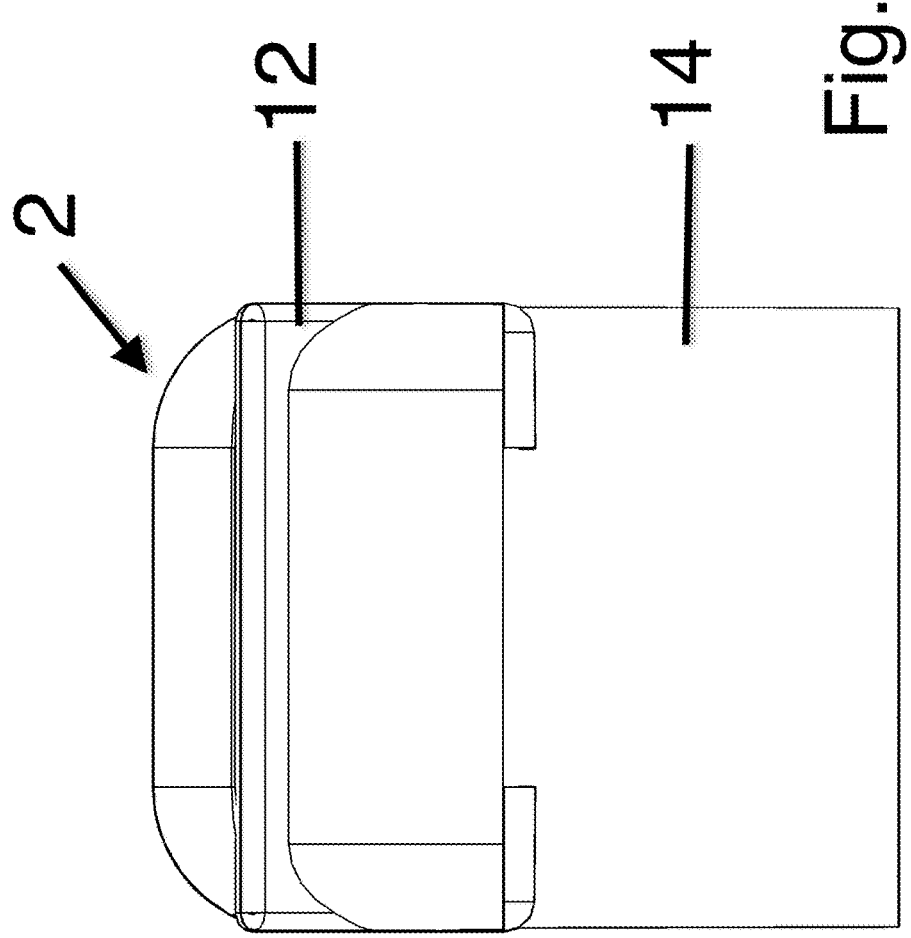

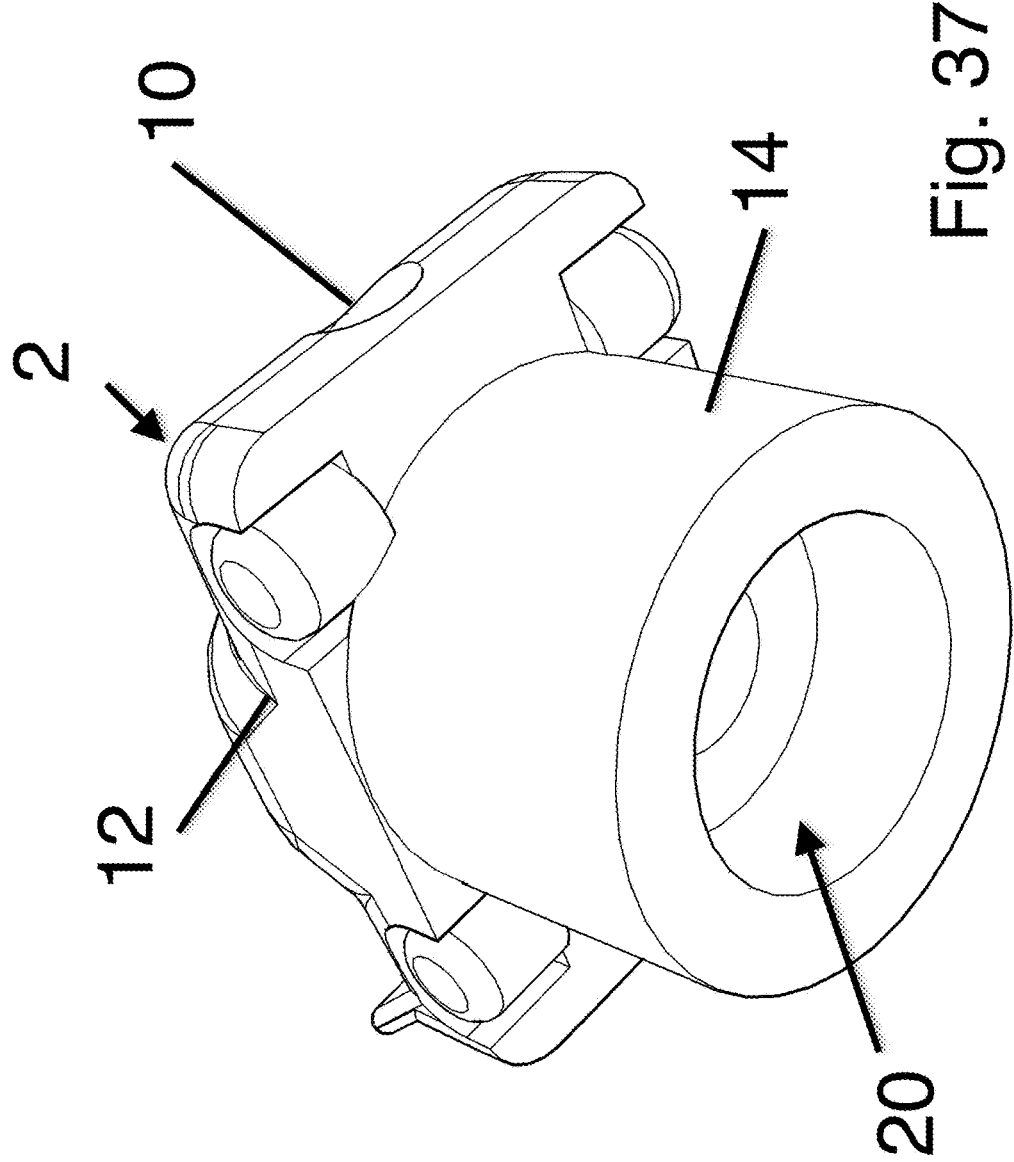

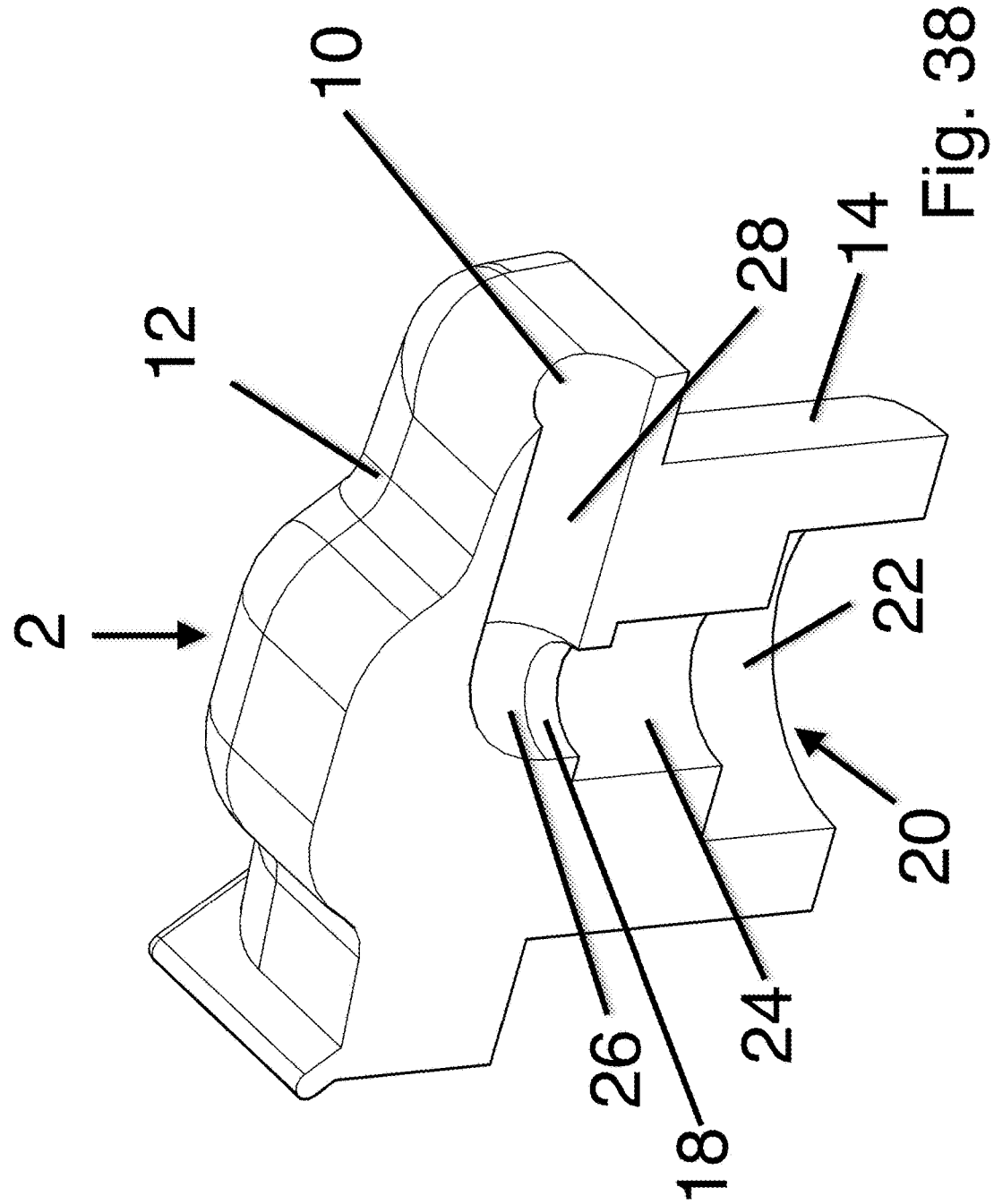

DEVICE FOR DIRECTING NEBULIZED VAPOR

CROSS REFERENCE TO RELATED APPLICATION

This application claims the benefit of U.S. Provisional Application No. 62/119,306, filed Feb. 23, 2015, which is incorporated herein by reference.

BACKGROUND

Conventionally, nebulizer masks are used to direct nebulized vapors into the respiratory tract of a human. However, for small children and infants, the inventor has determined that conventional masks utilized to direct a nebulized mixture are uncomfortable, disliked, and/or removed by children.

SUMMARY

A device for directing a nebulized mixture includes a receiver, disposed at lower end of the device, to receive a nebulizer, an exhaust port to expel a nebulized mixture from the device, and a passage to transport the nebulized mixture from the nebulizer to the exhaust port. The device has an external shape of a novelty.

There is also a method of directing a nebulized mixture. The method includes receiving the nebulized mixture by a device which has an external shape of a novelty, directing the nebulized mixture by the device, and exhausting towards the face of a person the nebulized mixture which has been directed by the device.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 32 is a perspective view from below of the device of FIG. 29;

FIG. 33 is a cross-sectional view of the device of FIG. 29 showing the interior passages;

FIG. 34 is an external perspective view of an example directing device for directing nebulized air;

FIG. 35 is a side view of the device of FIG. 34;

FIG. 36 is a rear view of the device of FIG. 34;

FIG. 37 is a perspective view from below of the device of FIG. 34; and

FIG. 38 is a cross-sectional view of the device of FIG. 34 showing the interior passages.

DETAILED DESCRIPTION OF THE PREFERRED EMBODIMENTS

Figure 1:
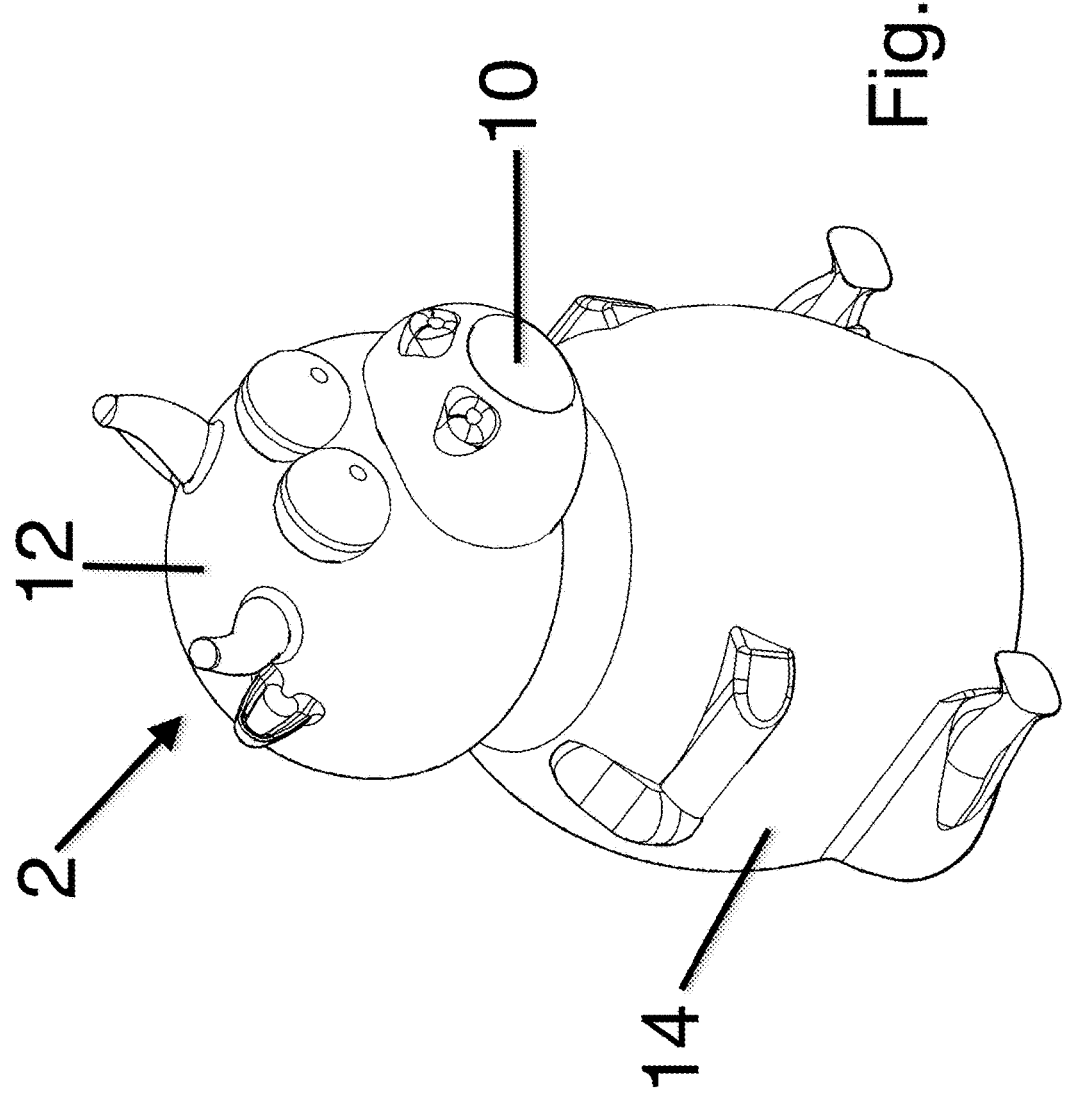
FIG. 1 is an external perspective view of an example directing device for directing nebulized air.

Referring now to the drawings, wherein like reference numerals designate identical or corresponding parts throughout the several views, a device 2 for directing nebulized vapor, referred to as a directing device and as shown in FIG. 1, is any type of novelty including animals, clowns, figurines, characters such as animated characters from a movie or television show, a doll house, a race car, or any device which would entertain a child or infant.

Exemplary nebulizers and systems are disclosed in U.S. Pat. Nos. 8,915,245, 8,950,393, 8,439,030, 8,397,712, 7,350,520, and 3,762,409, the contents of each of which are incorporated by reference. Any component of these prior nebulizer's and systems may be utilized with the directing device of the invention, as desired. The device 2 of FIG. 1 is, for example, a bull having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

Figure 2:
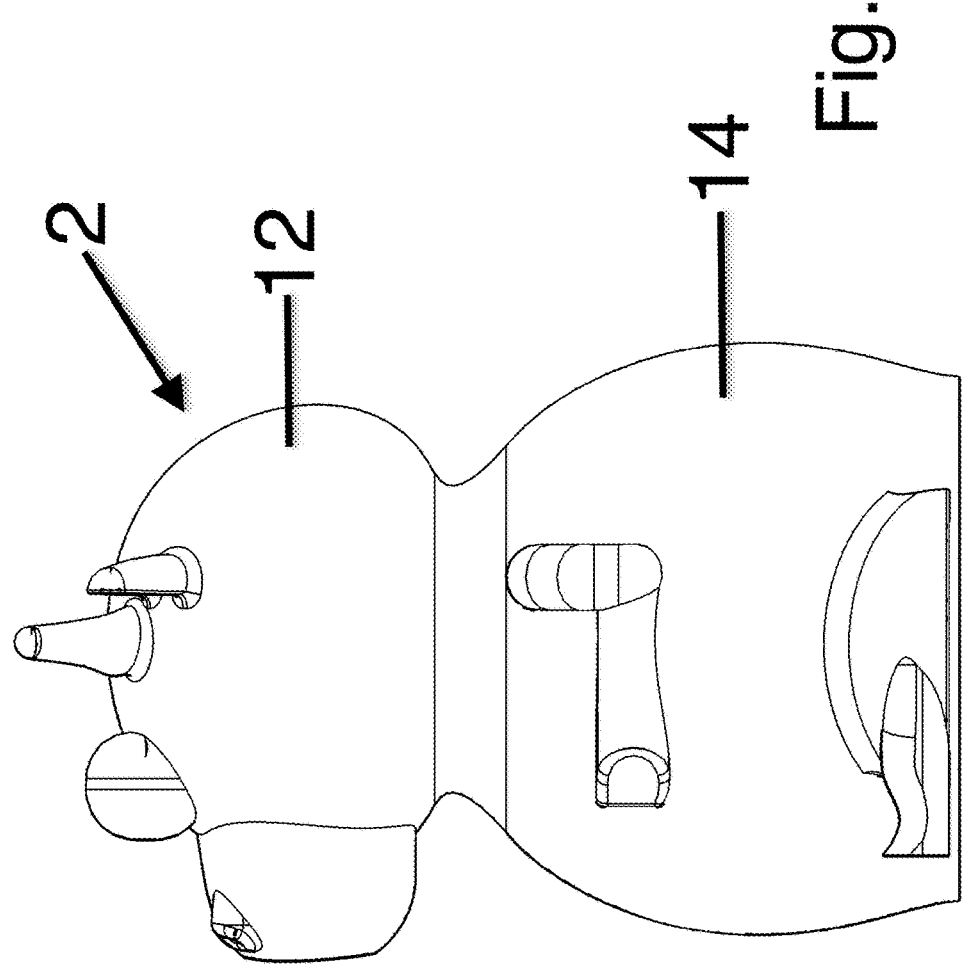
FIG. 2 is a side view of the device of FIG. 1.
Figure 3:
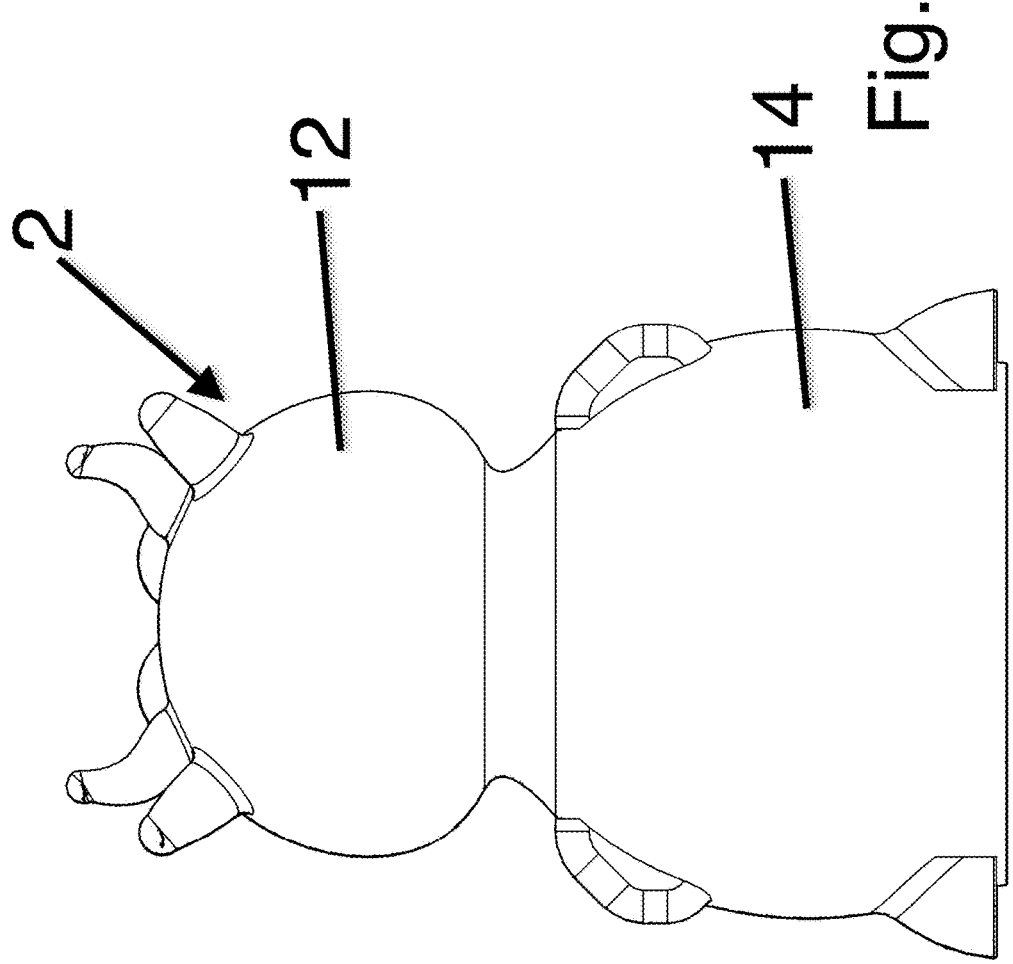
FIG. 3 is a rear view of the device of FIG. 1.

FIG. 2 is a side view of the device 2 of FIG. 1, and FIG. 3 is a rear view of the device 2 of FIG. 1.

Figure 4:
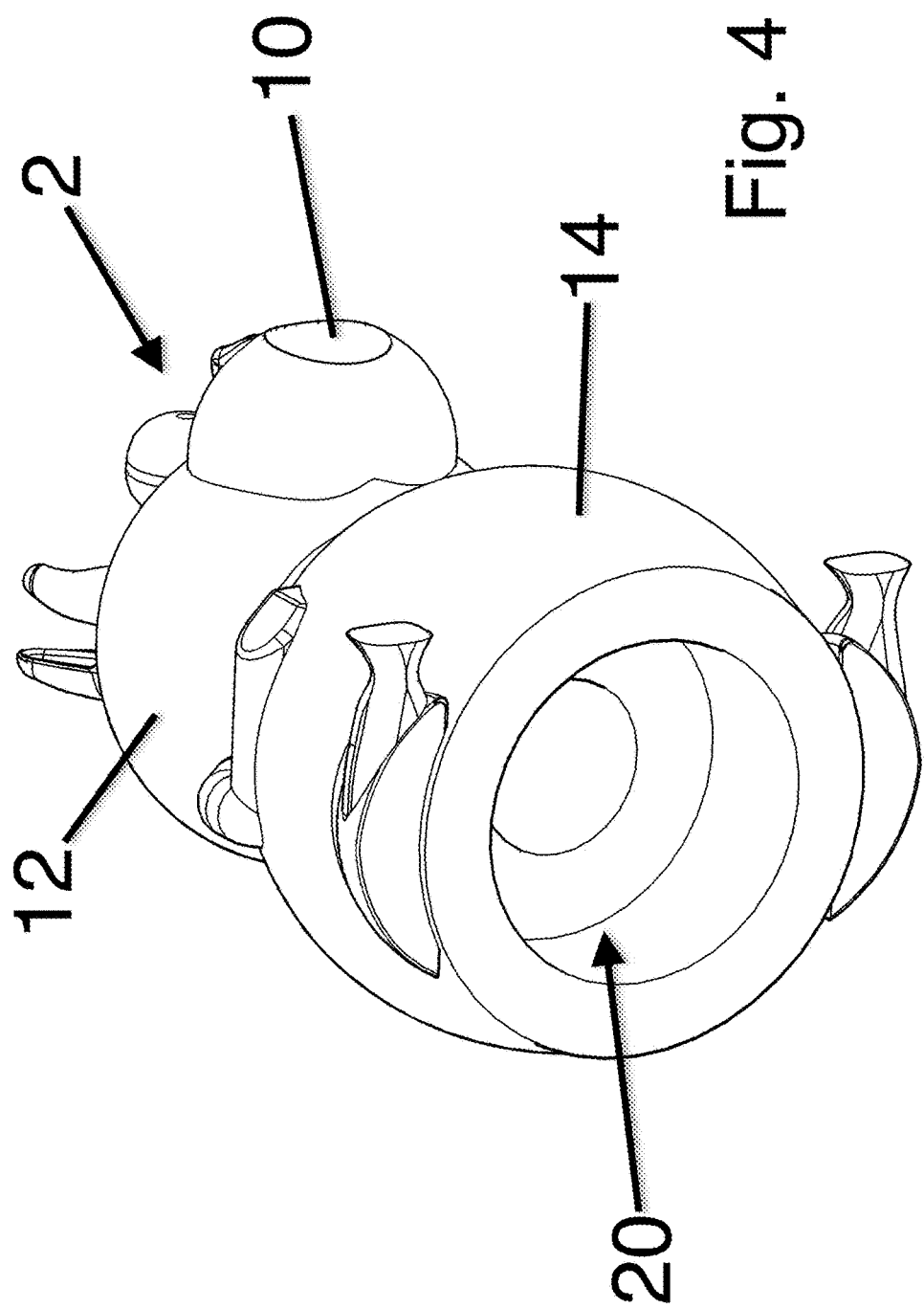
FIG. 4 is a perspective view from below of the device of FIG. 1.
Figure 5:
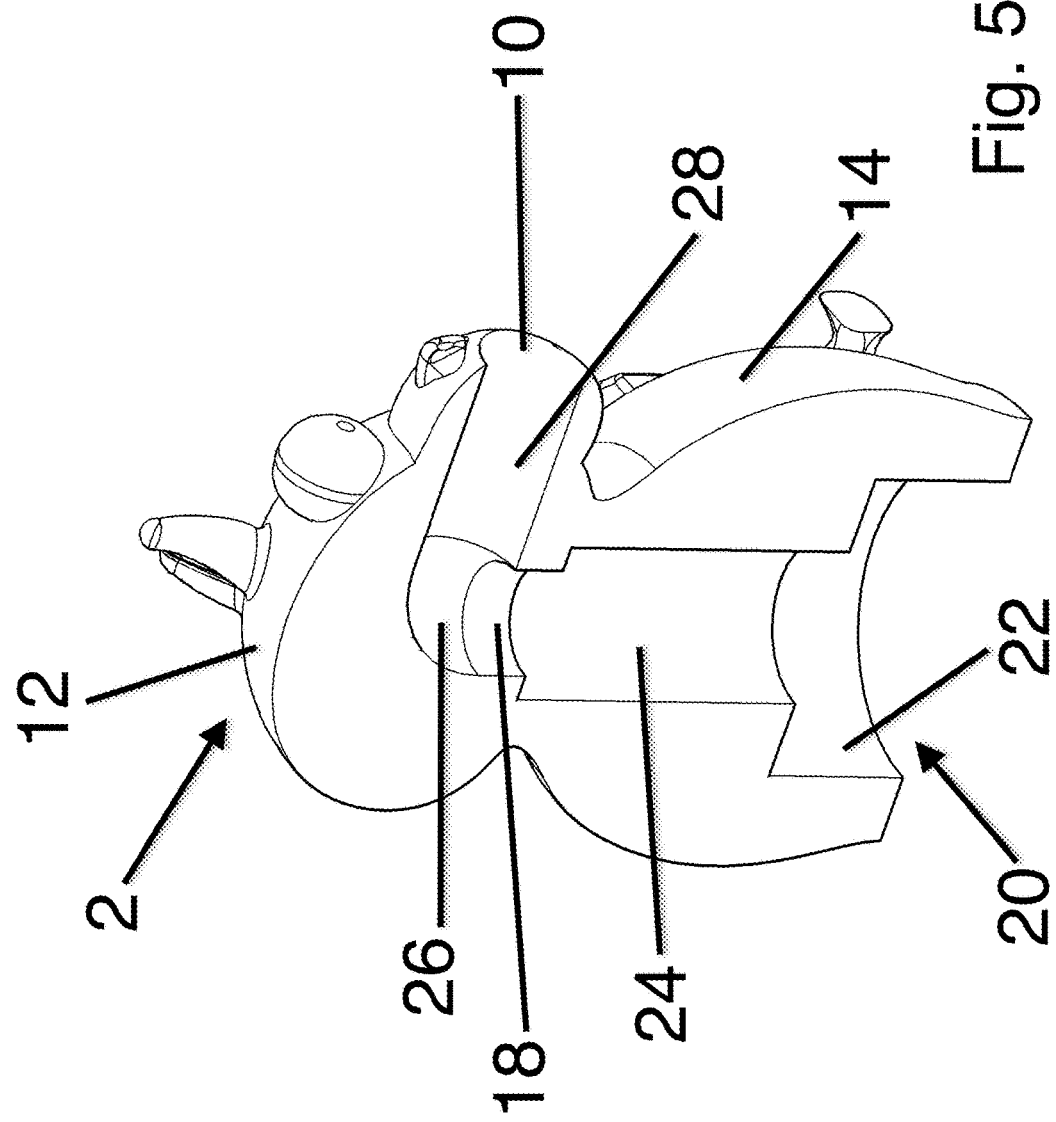
FIG. 5 is a cross-sectional view of the device of FIG. 1 showing the interior passages.

FIG. 4 is a perspective view from below of the device 2 of FIG. 1. In this Figure, the receiver 20 is visible and receives a nebulizer 30. FIG. 5 is a cross-sectional view of the device 2 of FIG. 1 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, adhesive and/or glue, a latch, or a twist-lock system in order to retain the nebulizer within the receiver, for example.

As shown in the cross-sectional view of FIG. 5, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

Figure 6:
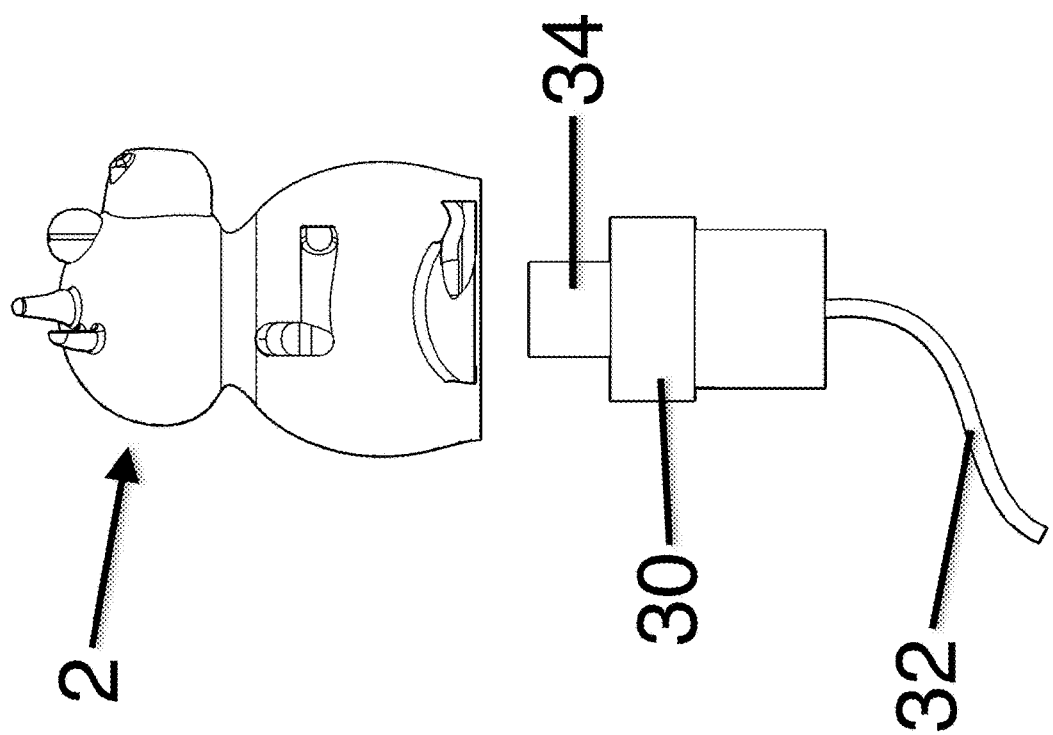
FIG. 6 illustrates the device of FIG. 1 disposed above a nebulizer.
Figure 7:
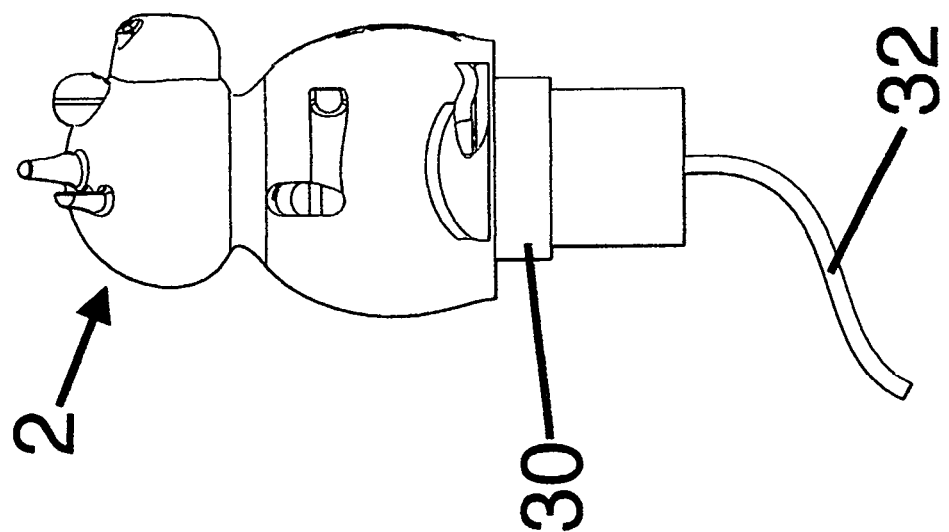
FIG. 7 illustrates the device of FIG. 1 having the nebulizer mounted thereto.

FIG. 6 illustrates the nebulizer 30 including a connection section 34 which frictionally mates with the receiver 20. A nebulizer includes a chamber for holding a liquid such as a medicine which is to be nebulized in order to become a nebulized mixture which is inhaled by the infant or child. The nebulizer can nebulize the medicine or other liquid using air received from the air hose 32 which may be connected to any type of air compressor or air source. FIG. 7 illustrates the nebulizer 30 mounted to the receiver 20 of the device 2.

Figure 8:
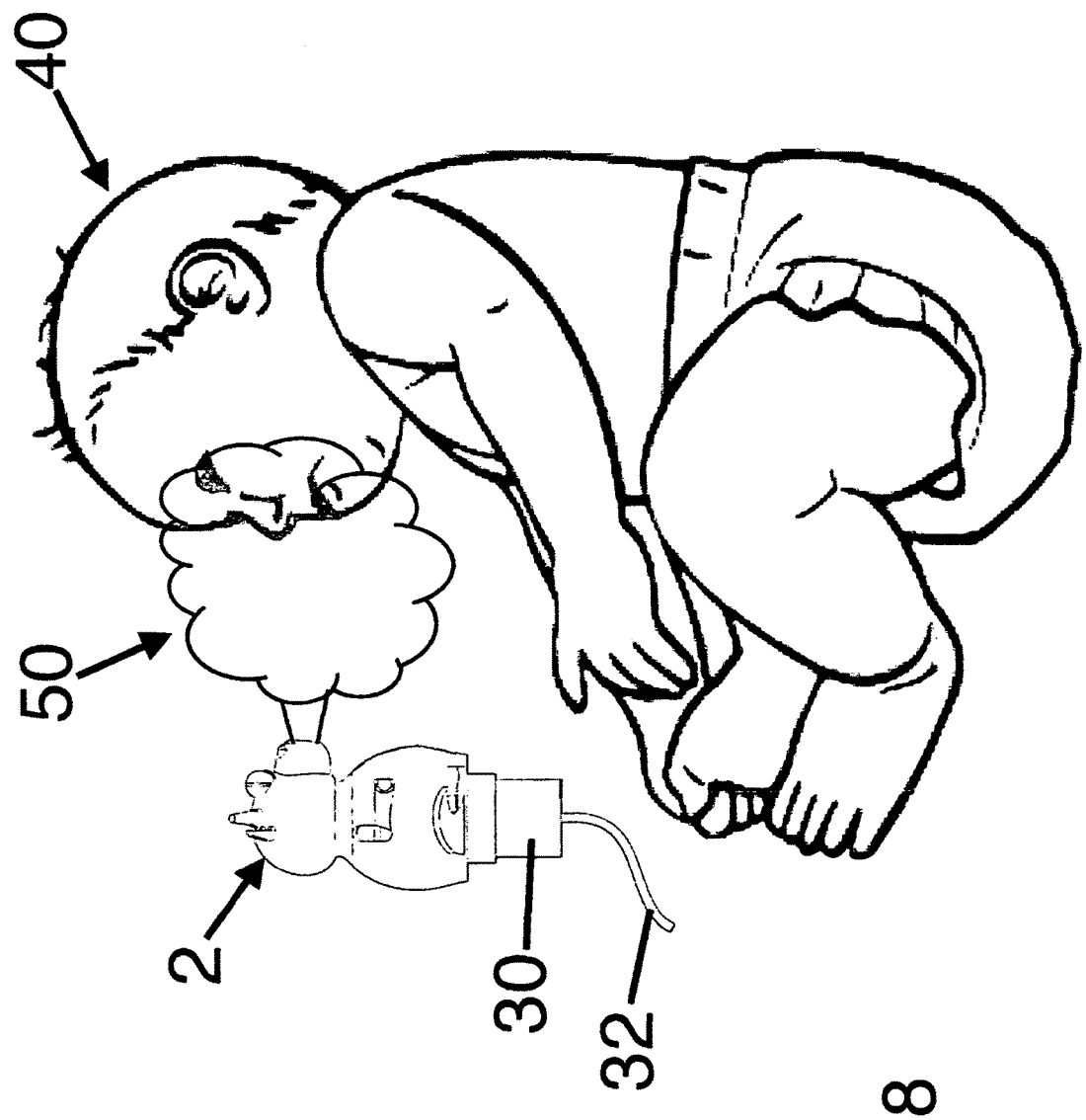
FIG. 8 illustrates the device of FIG. 1 exhausting nebulized fluid towards a child.

FIG. 8 illustrates the device 2 directing a nebulized mixture 50 to the face of an infant or child 40. The device 2 can be held by an adult, placed in a stand, or held by the person receiving the nebulized mixture.

Figure 9:
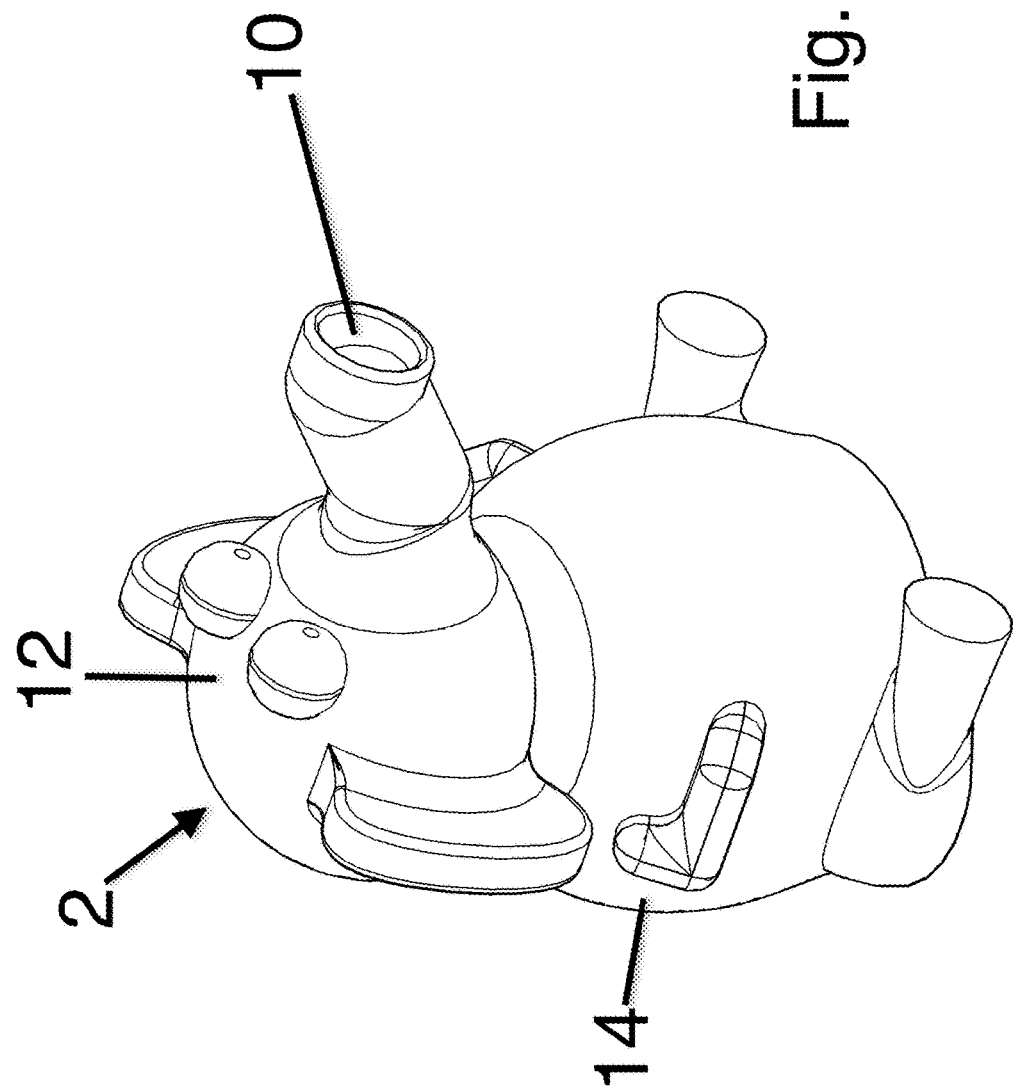
FIG. 9 is an external perspective view of an example directing device for directing nebulized air.

The device 2 of FIG. 9 is, for example, an elephant having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

Figure 10:
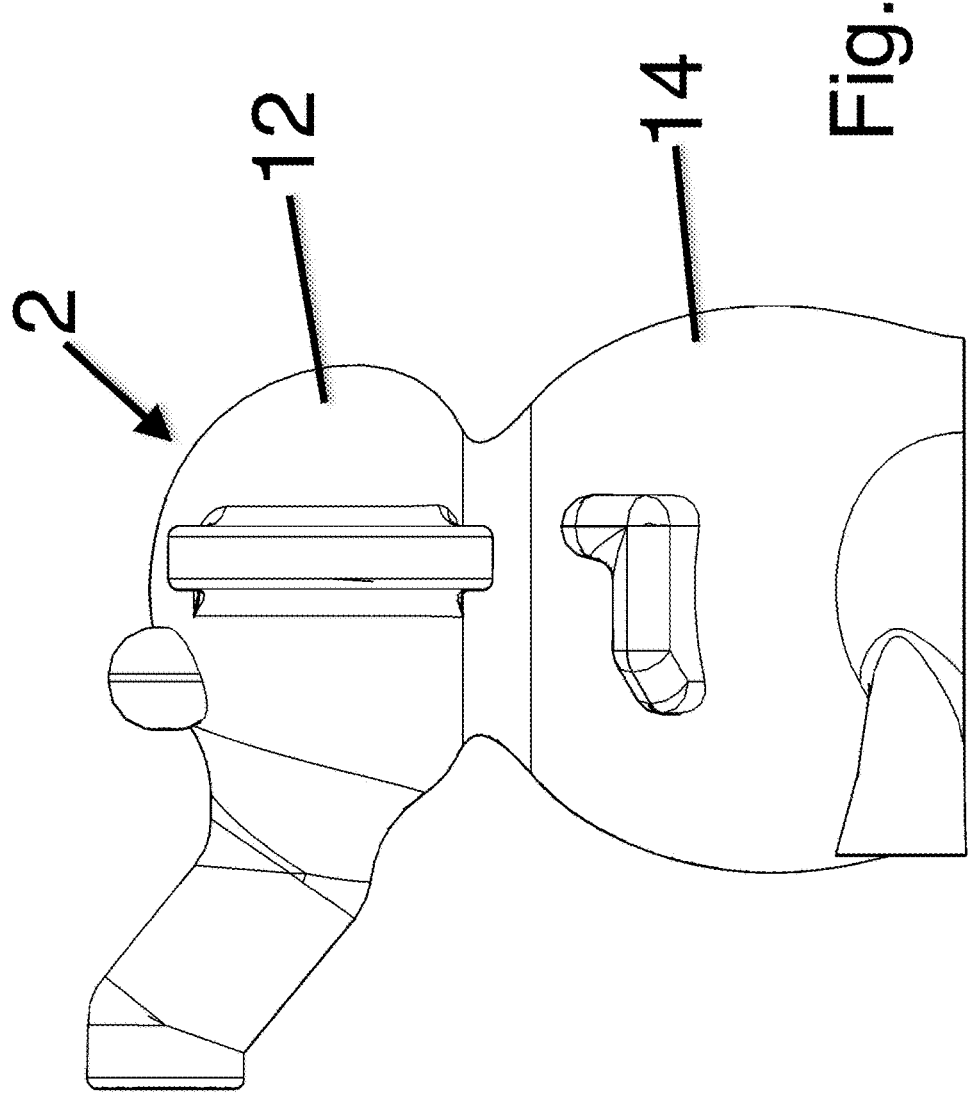
FIG. 10 is a side view of the device of FIG. 9.
Figure 11:
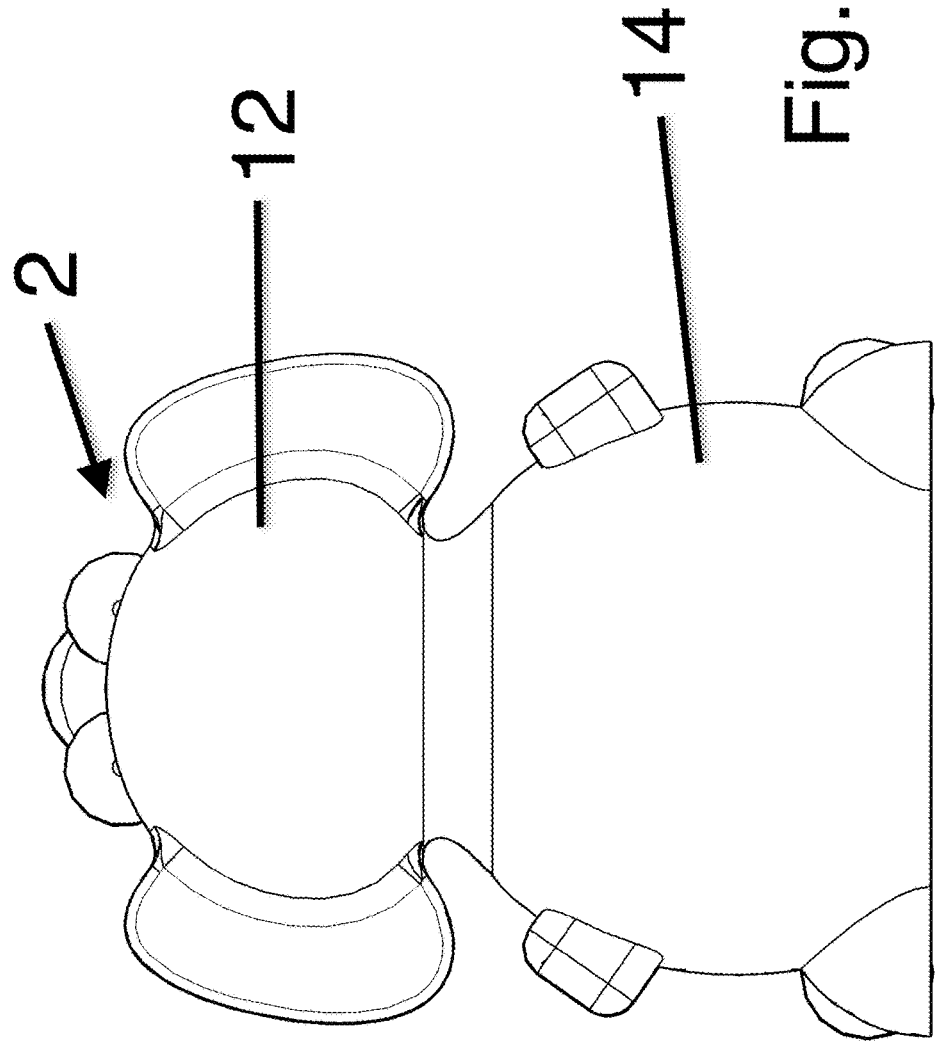
FIG. 11 is a rear view of the device of FIG. 9.

FIG. 10 is a side view of the device 2 of FIG. 9, and FIG. 11 is a rear view of the device 2 of FIG. 9.

Figure 12:
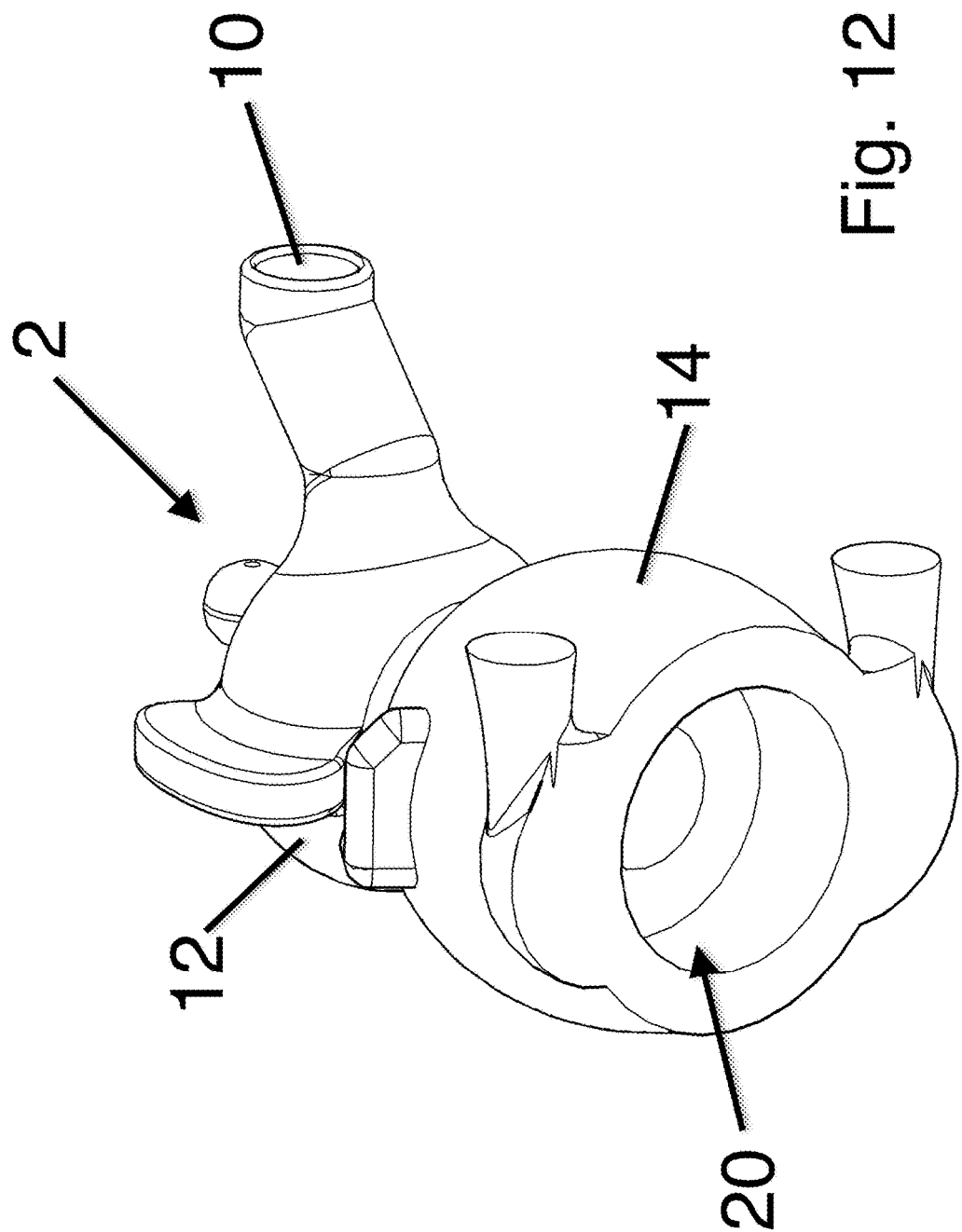
FIG. 12 is a perspective view from below of the device of FIG. 9.
Figure 13:
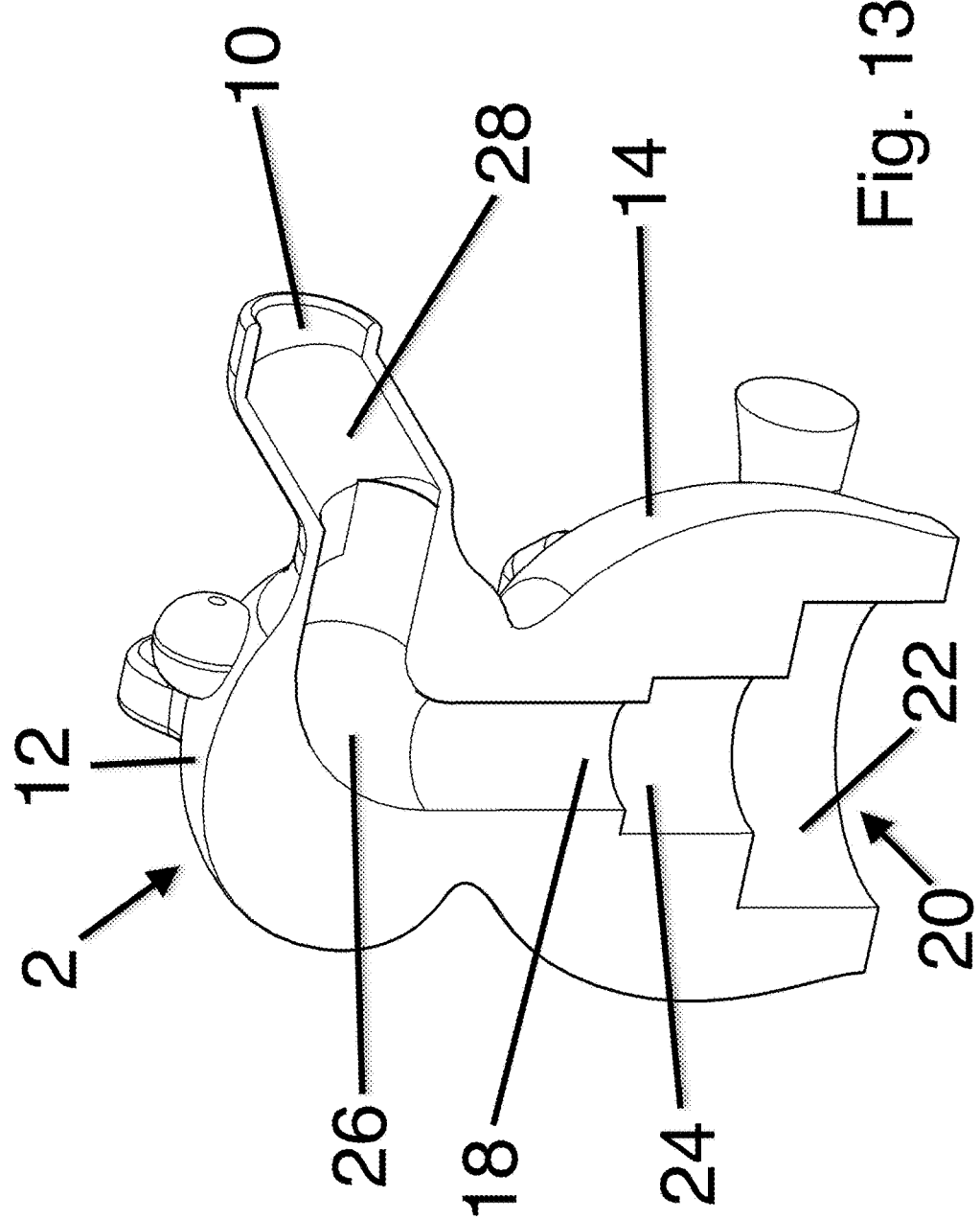
FIG. 13 is a cross-sectional view of the device of FIG. 9 showing the interior passages.

FIG. 12 is a perspective view from below of the device 2 of FIG. 9. In this Figure, the receiver 20 is visible and receives a nebulizer 30. FIG. 13 is a cross-sectional view of the device 2 of FIG. 9 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 13, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

Figure 14:
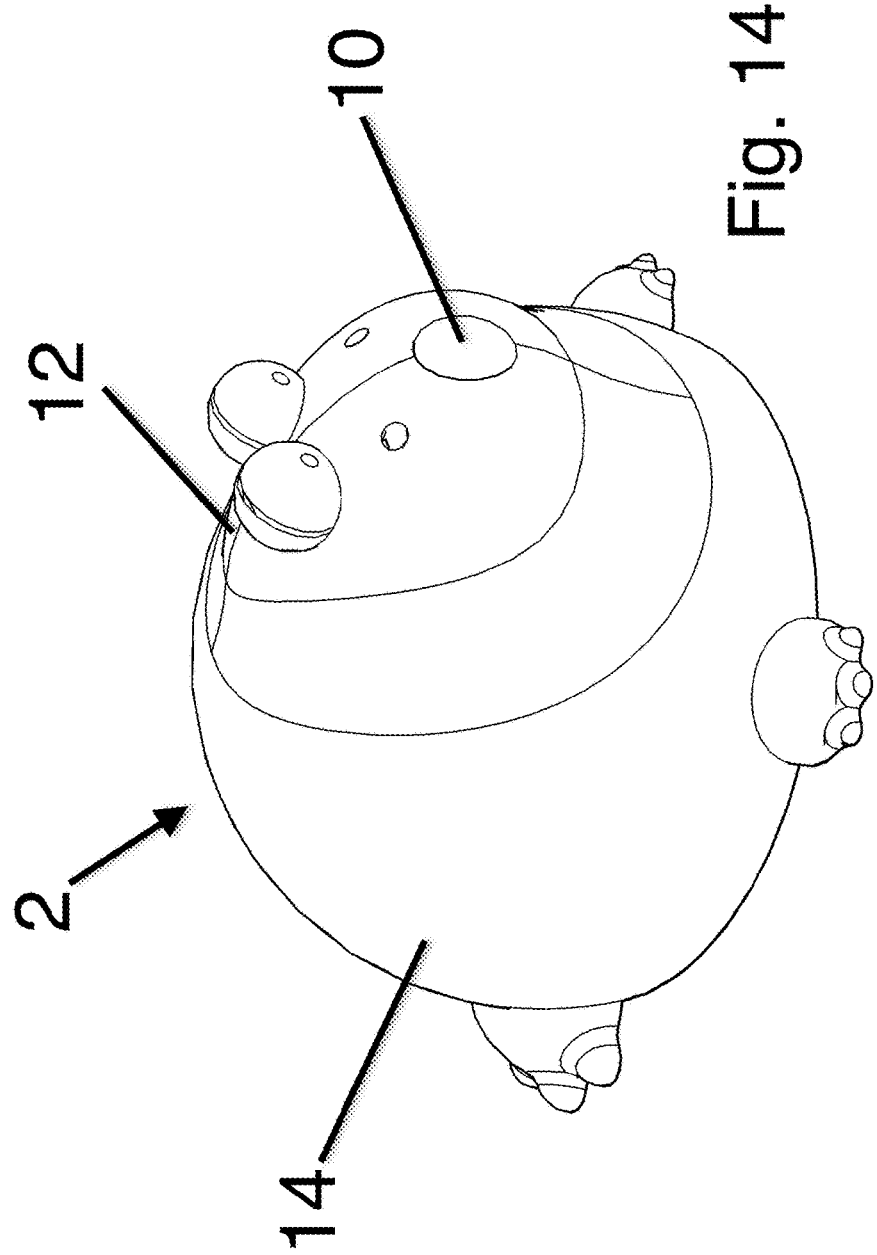
FIG. 14 is an external perspective view of an example directing device for directing nebulized air.

The device 2 of FIG. 14 is, for example, a frog having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

Figure 15:
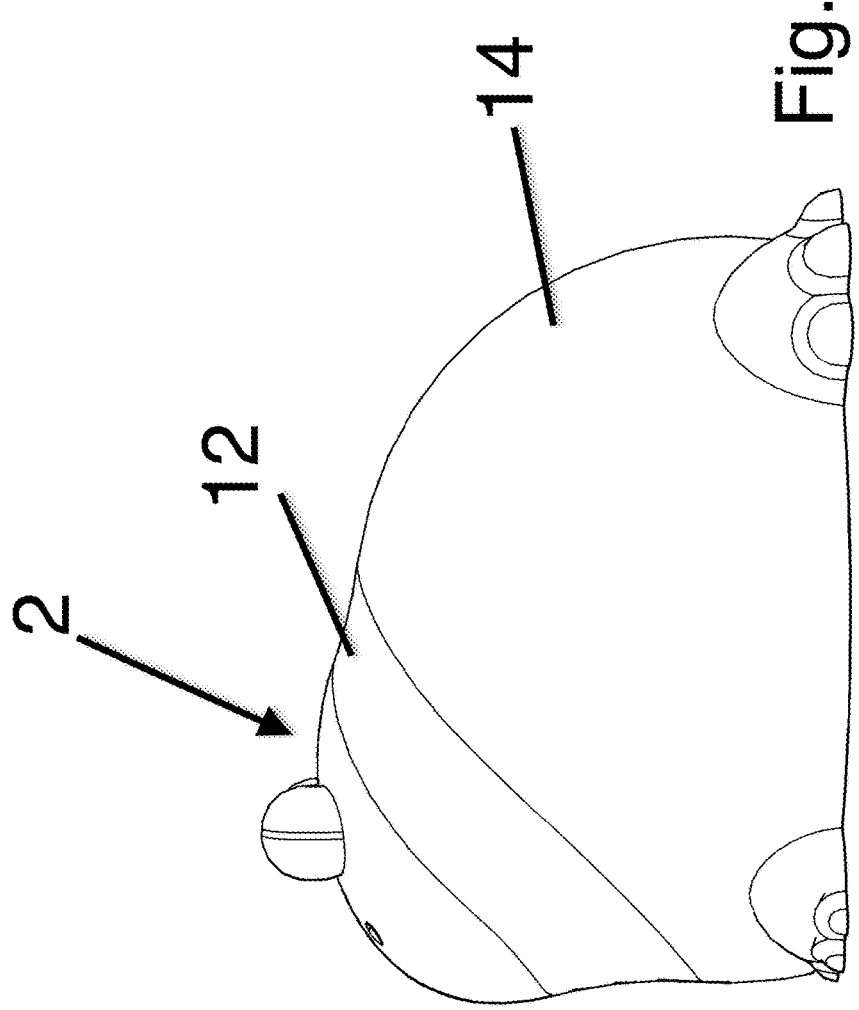
FIG. 15 is a side view of the device of FIG. 14.
Figure 16:
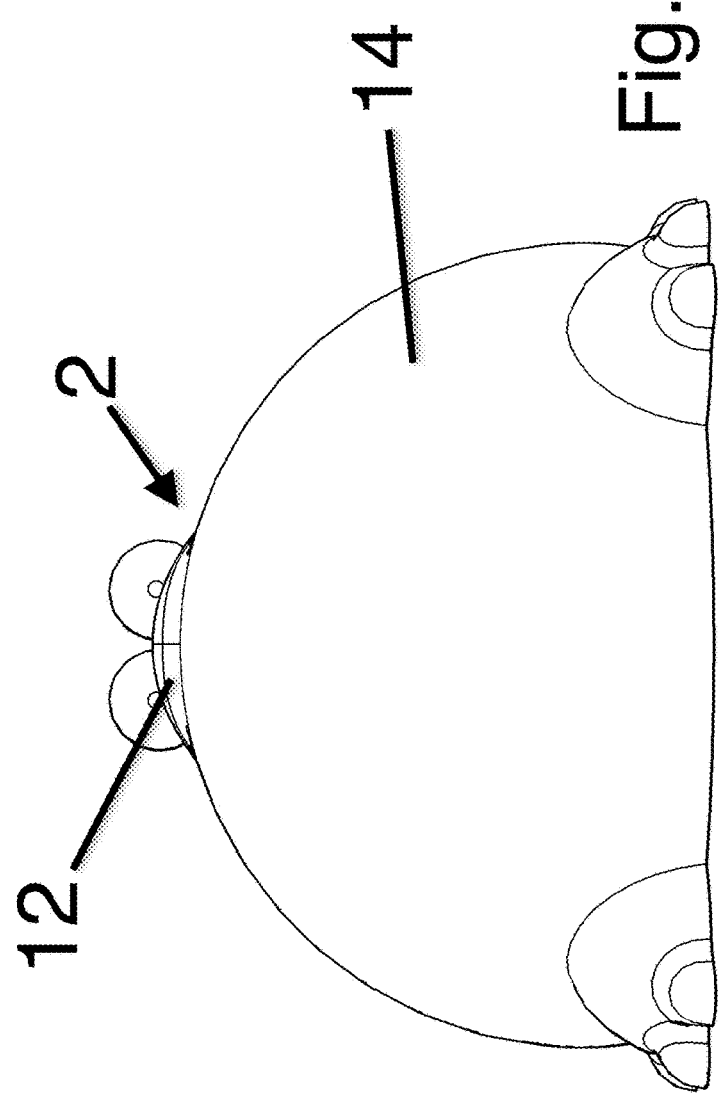
FIG. 16 is a rear view of the device of FIG. 14.

FIG. 15 is a side view of the device 2 of FIG. 14, and FIG. 16 is a rear view of the device 2 of FIG. 14.

Figure 17:
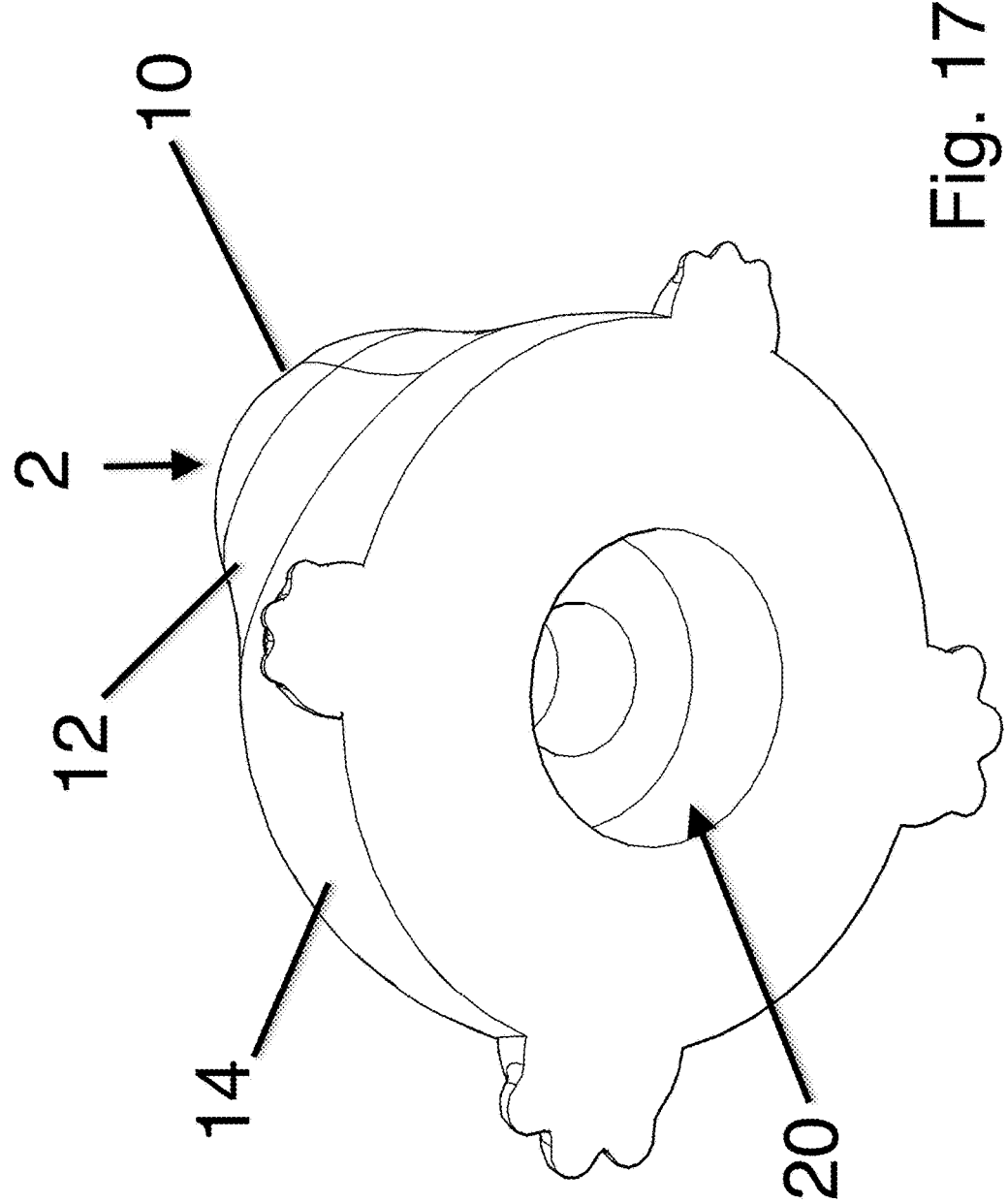
FIG. 17 is a perspective view from below of the device of FIG. 14.
Figure 18:
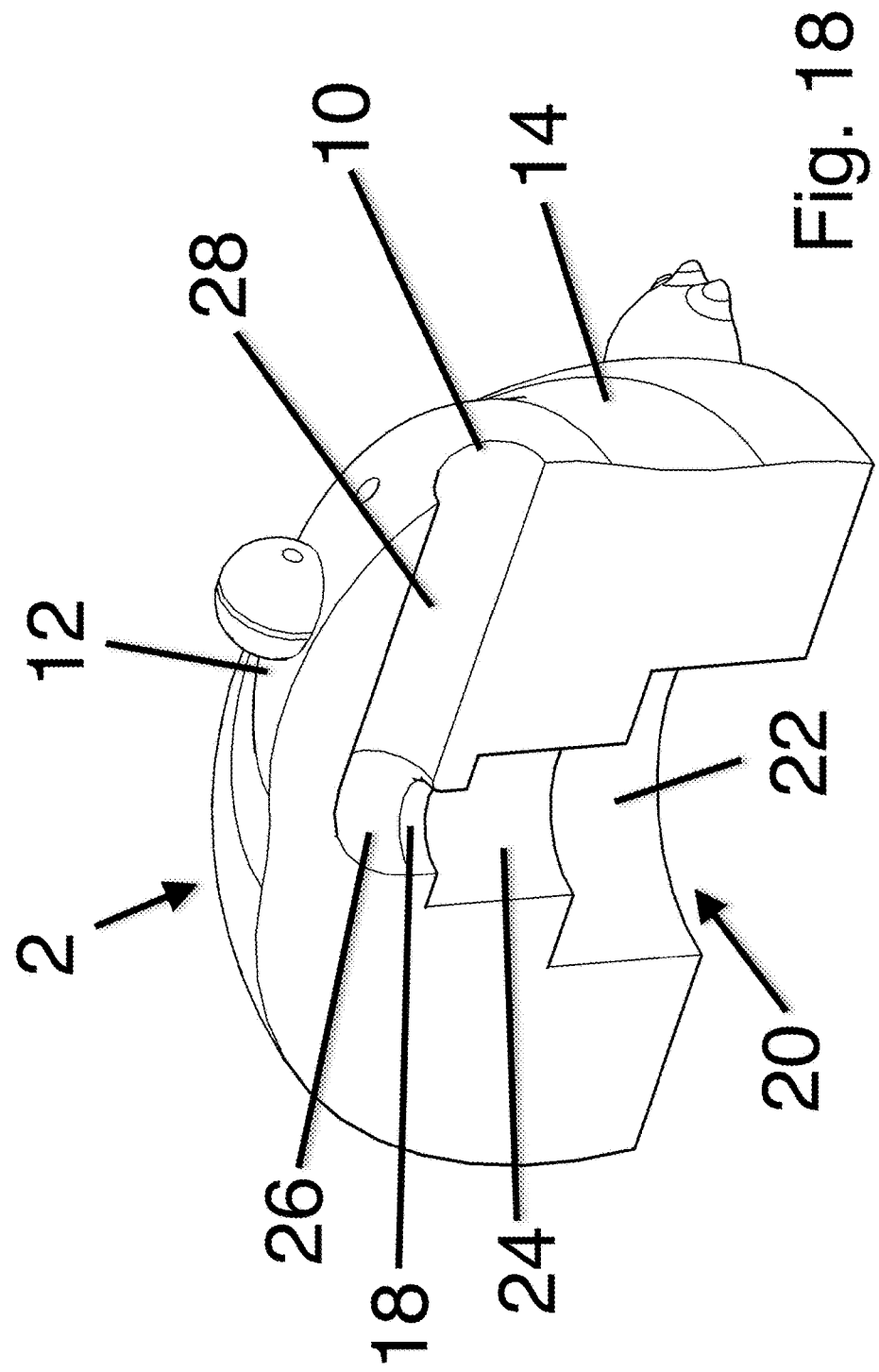
FIG. 18 is a cross-sectional view of the device of FIG. 14 showing the interior passages.

FIG. 17 is a perspective view from below of the device 2 of FIG. 14. In this Figure, the receiver 20 is visible and receives a nebulizer 30. FIG. 18 is a cross-sectional view of the device 2 of FIG. 14 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 18, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

Figure 19:
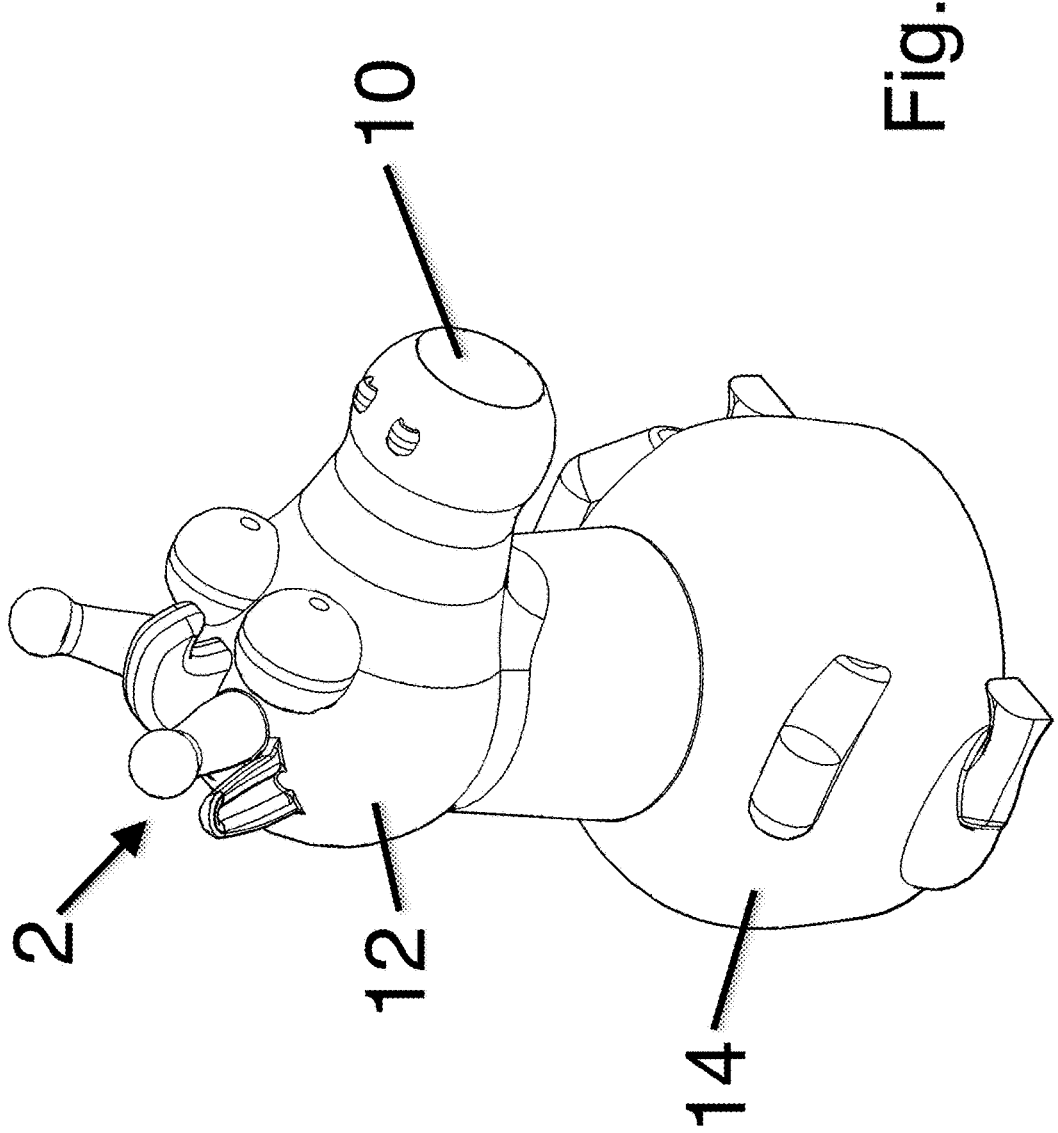
FIG. 19 is an external perspective view of an example directing device for directing nebulized air.

The device 2 of FIG. 19 is, for example, a giraffe having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

Figure 20:
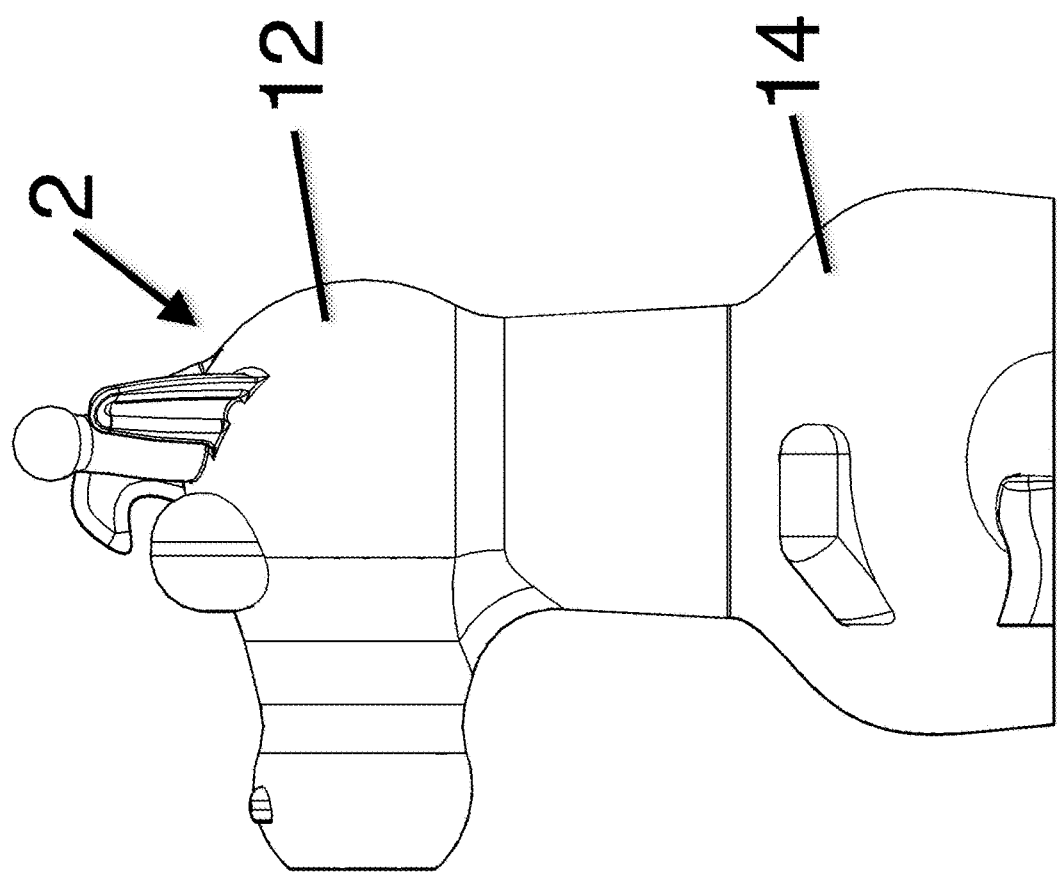
FIG. 20 is a side view of the device of FIG. 19.
Figure 21:
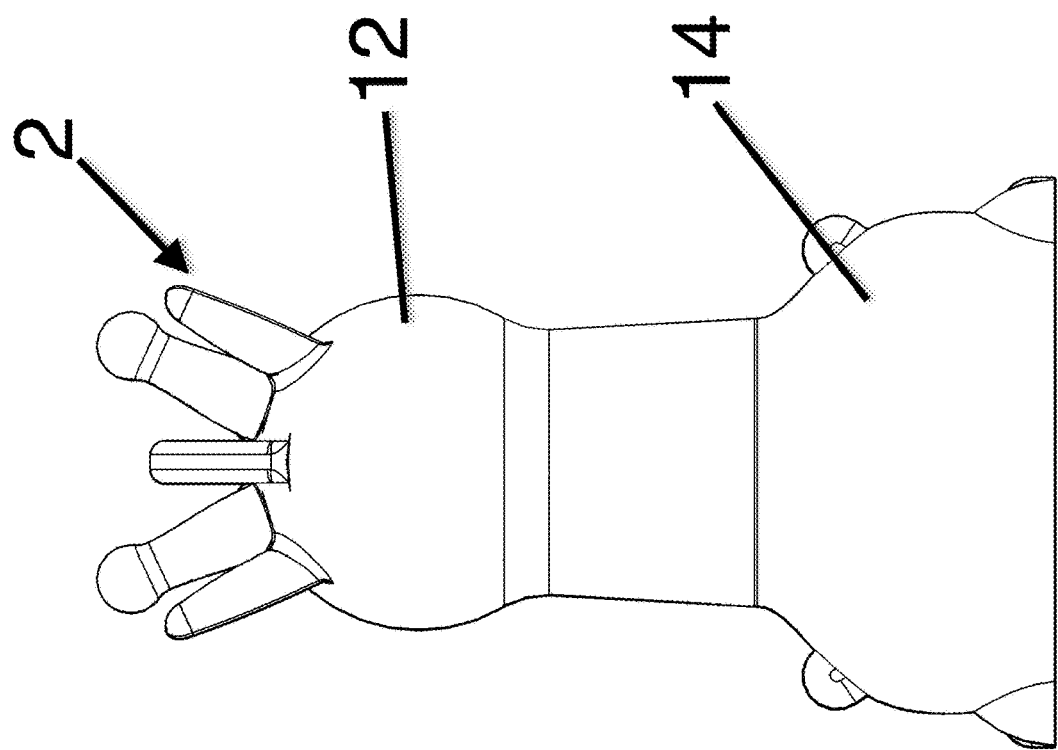
FIG. 21 is a rear view of the device of FIG. 19.
Figure 22:
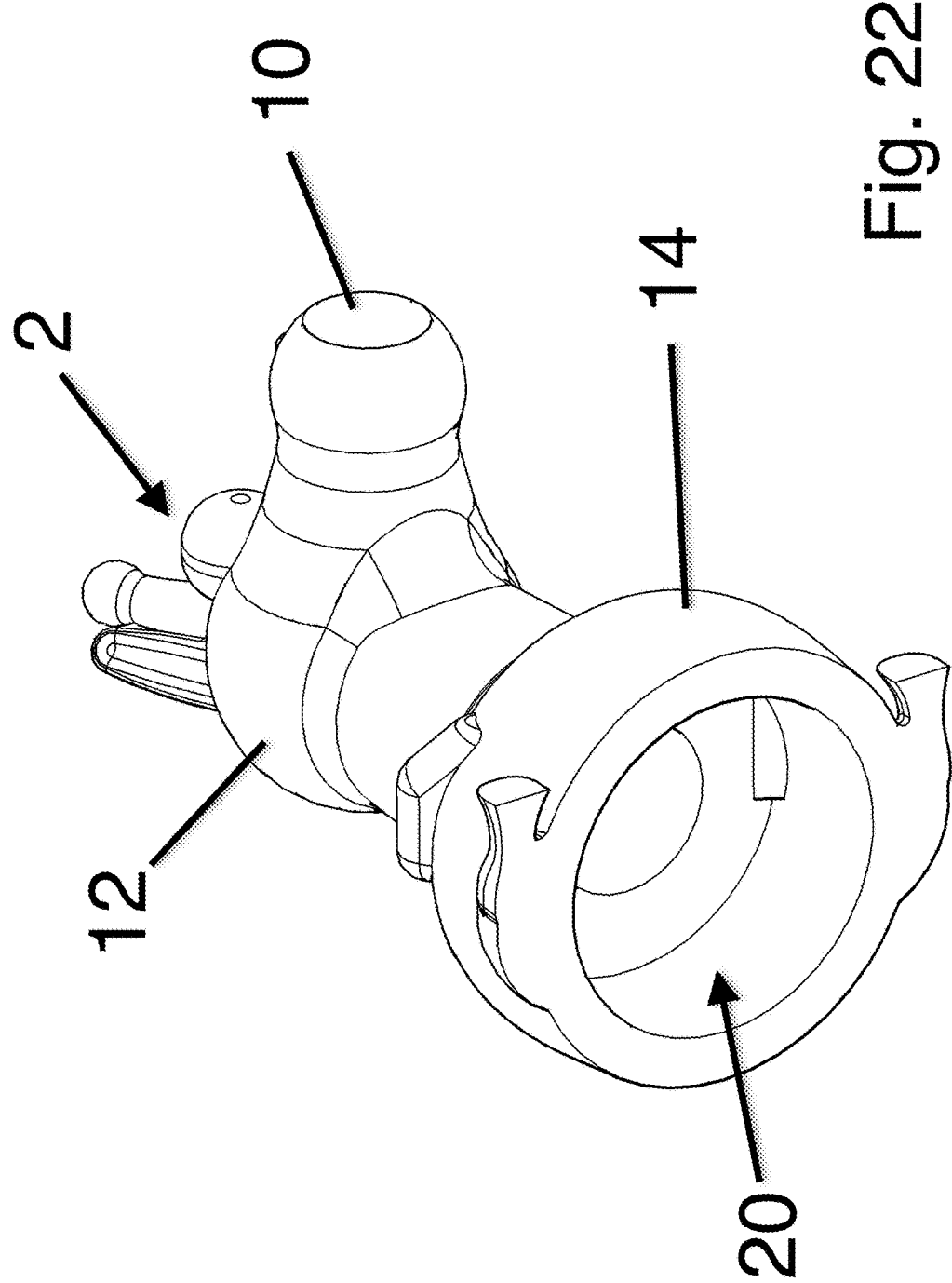
FIG. 22 is a perspective view from below of the device of FIG. 19.
Figure 23:
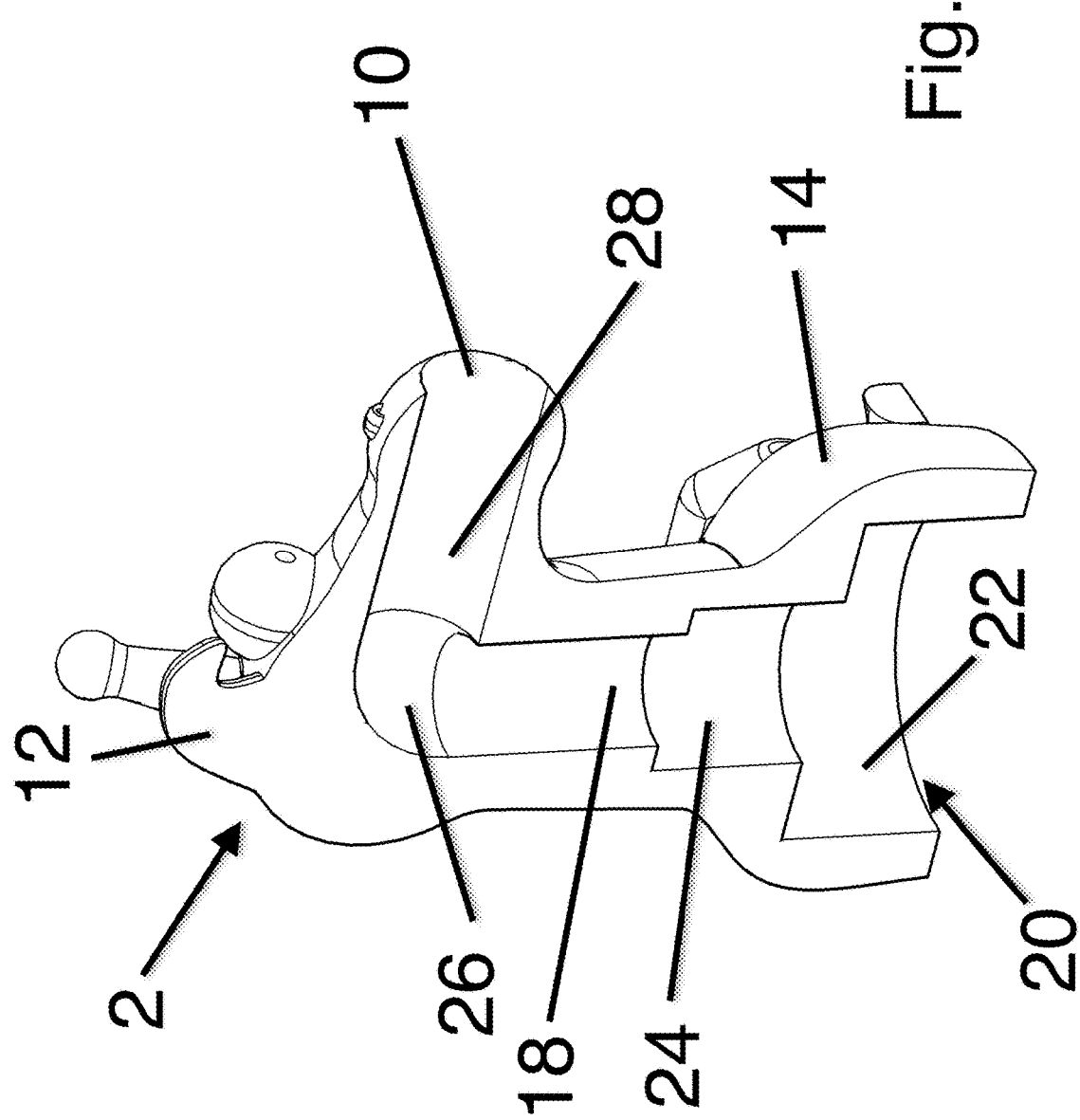
FIG. 23 is a cross-sectional view of the device of FIG. 19 showing the interior passages.
Figure 24:
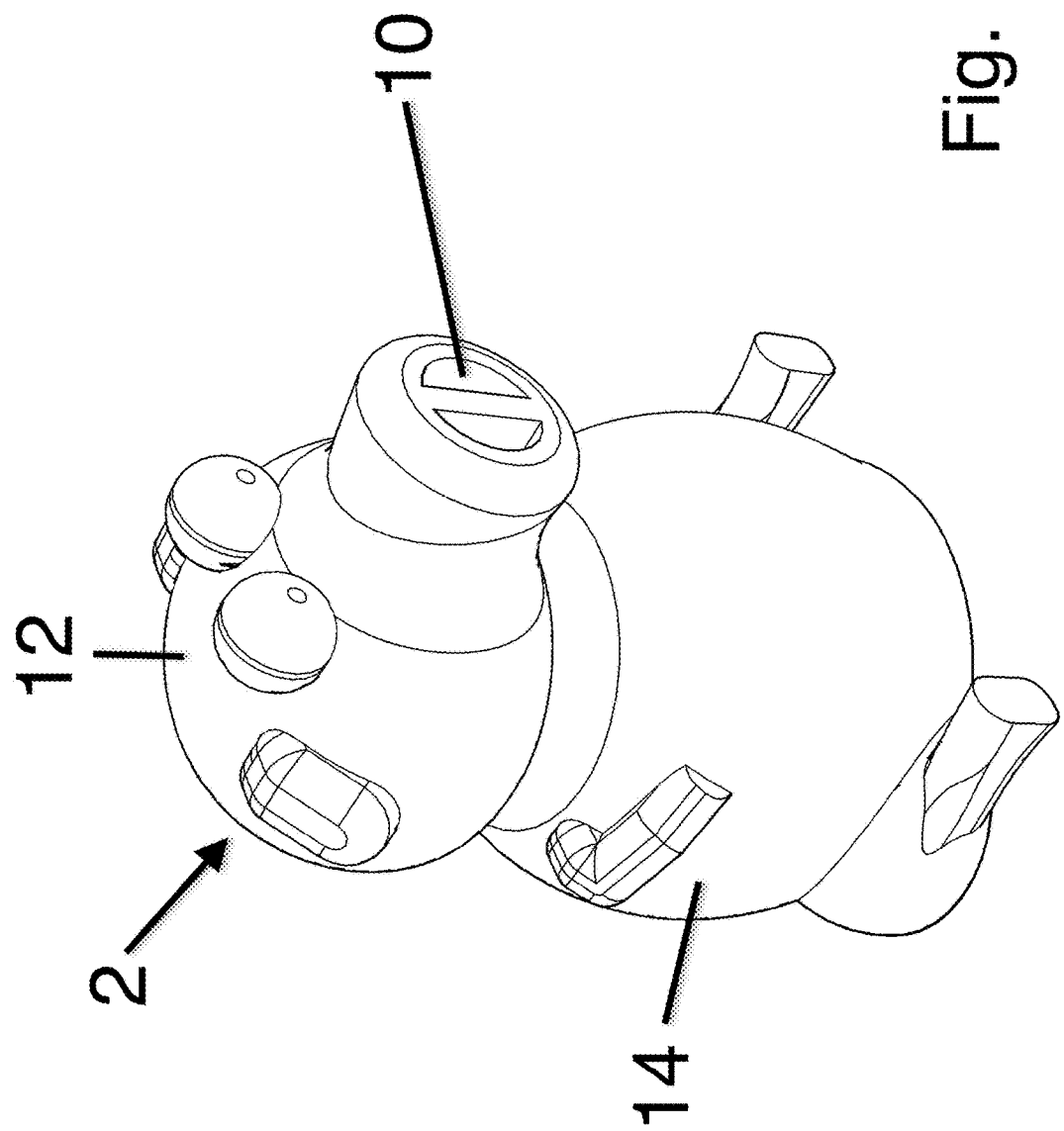
FIG. 24 is an external perspective view of an example directing device for directing nebulized air.
Figure 25:
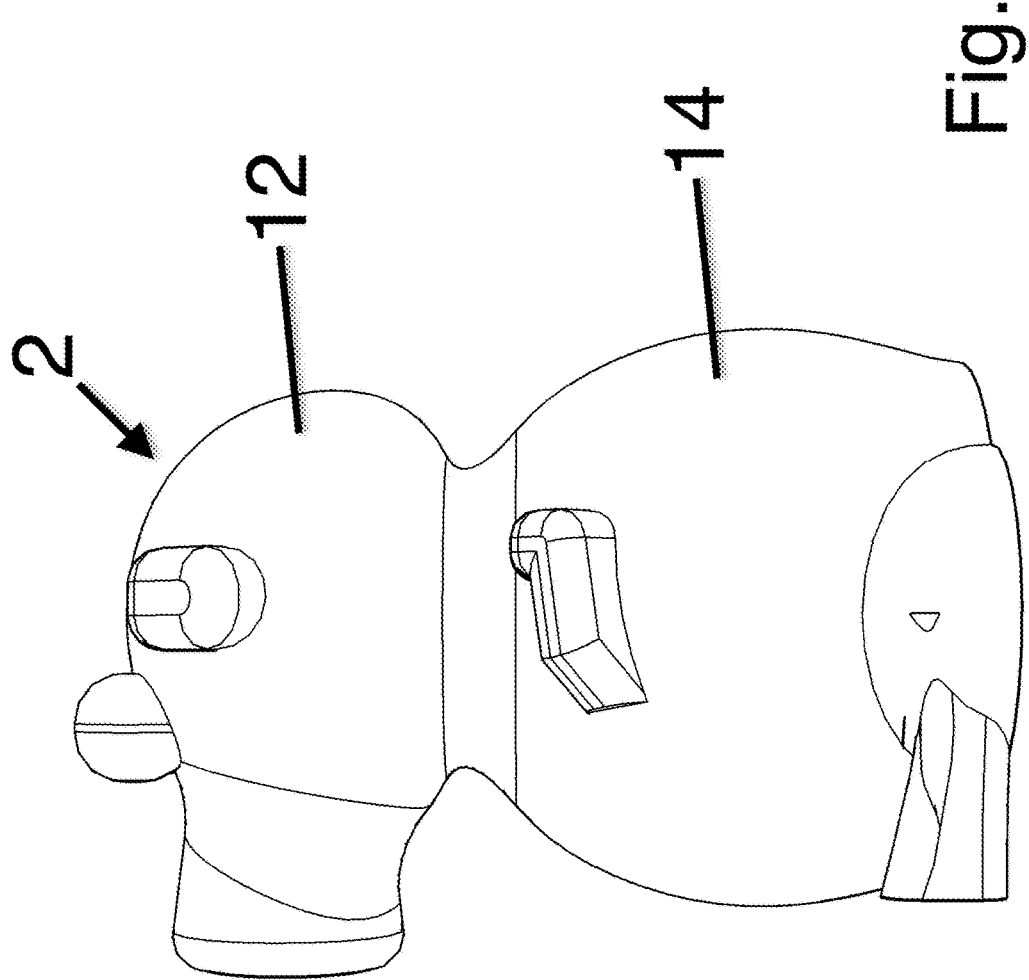
FIG. 25 is a side view of the device of FIG. 24.
Figure 26:
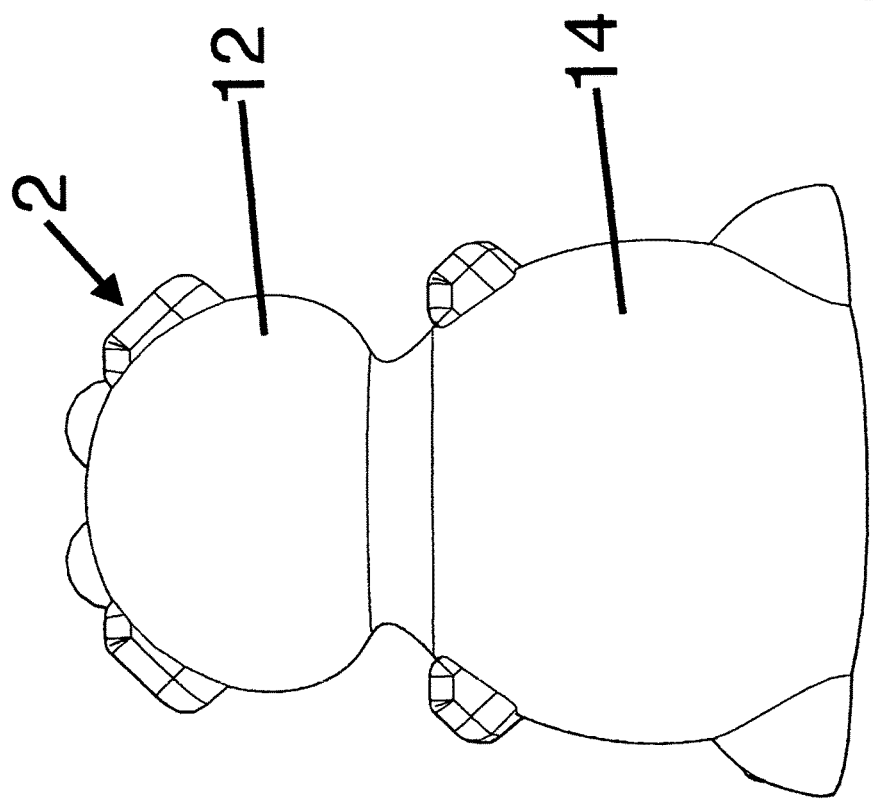
FIG. 26 is a rear view of the device of FIG. 24.
Figure 27:
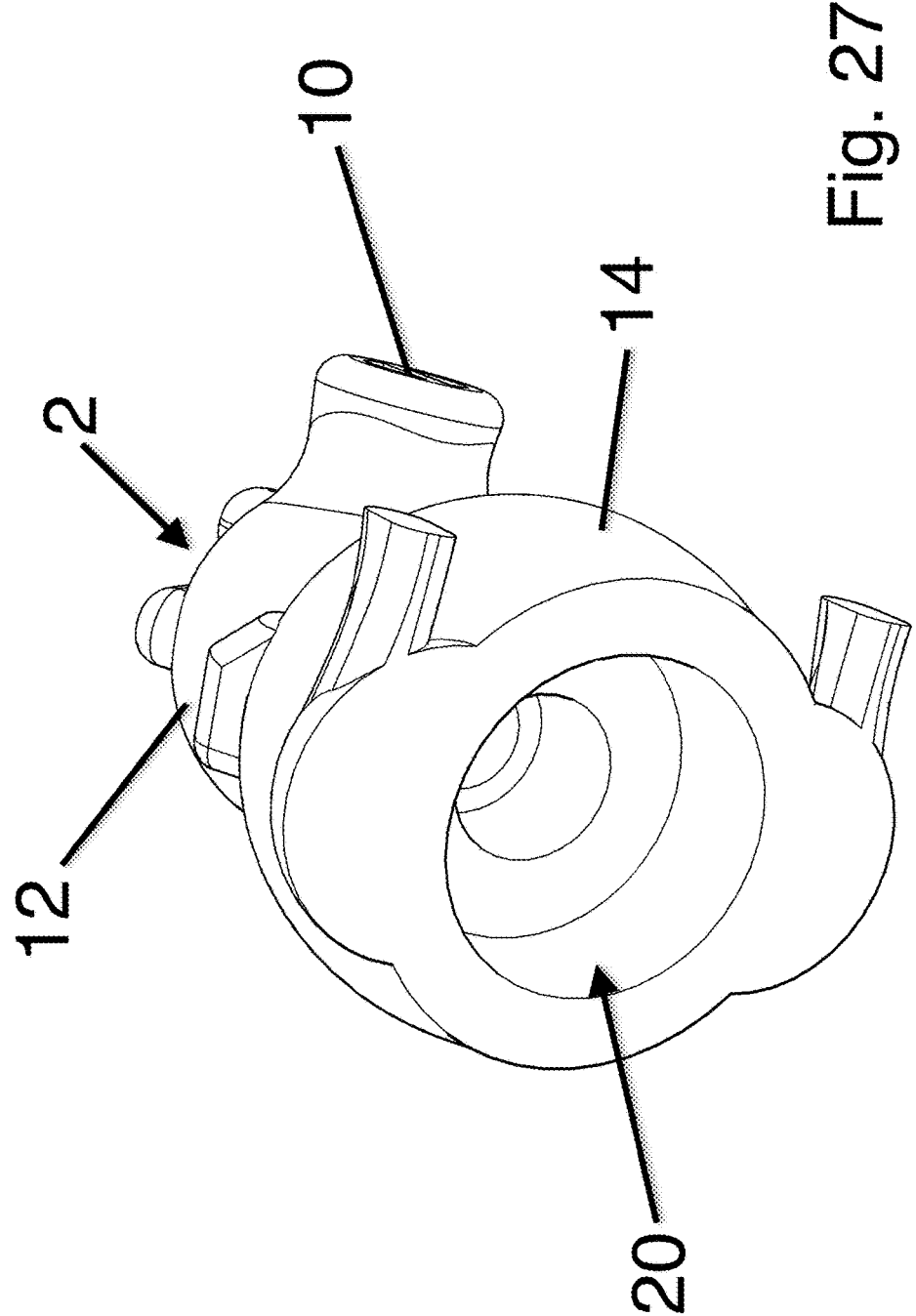
FIG. 27 is a perspective view from below of the device of FIG. 24.
Figure 28:
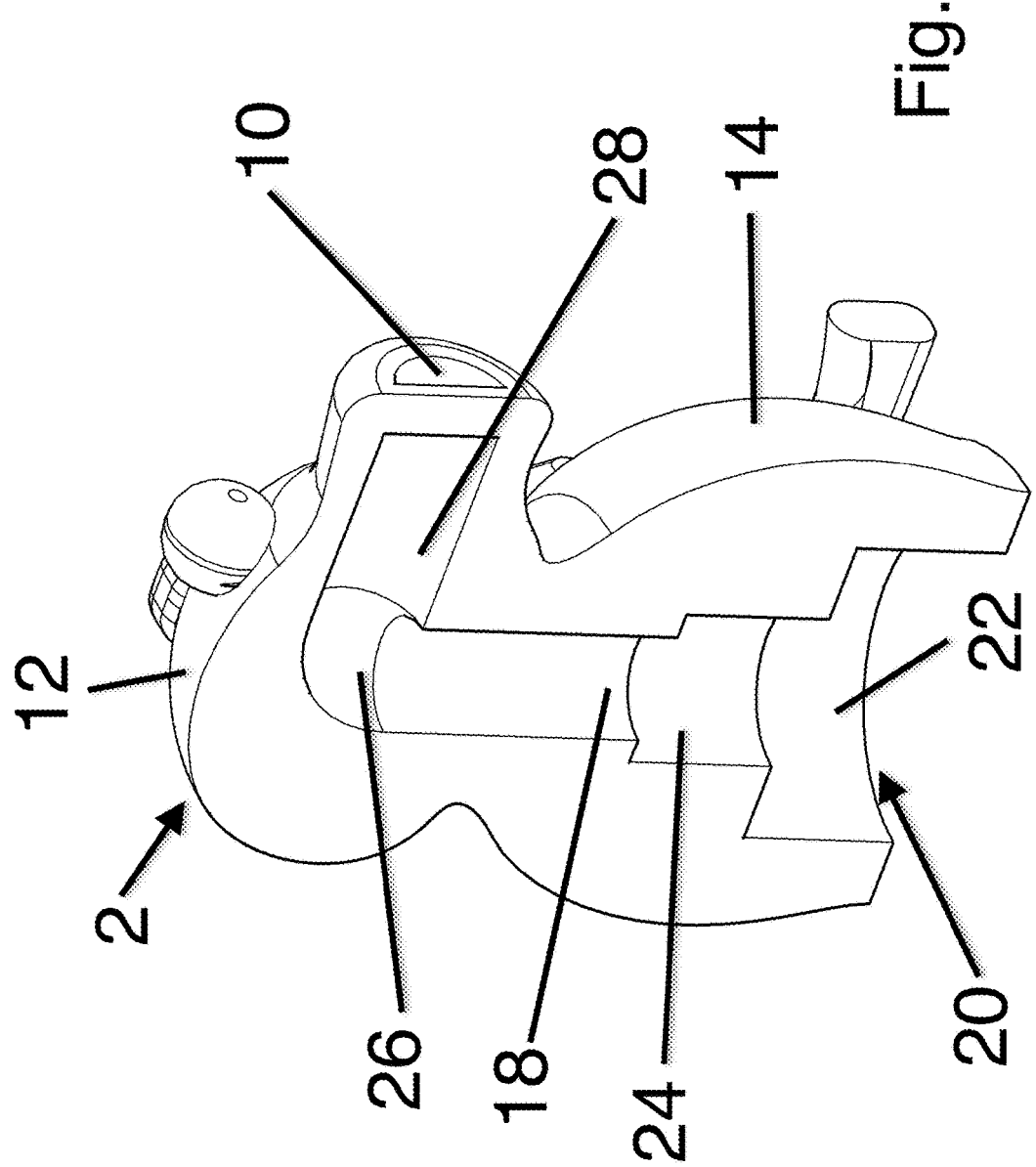
FIG. 28 is a cross-sectional view of the device of FIG. 24 showing the interior passages.

FIG. 20 is a side view of the device 2 of FIG. 19, and FIG. 21 is a rear view of the device 2 of FIG. 19.

FIG. 22 is a perspective view from below of the device 2 of FIG. 19. In this Figure, the receiver 20 is visible and receives a nebulizer 30. FIG. 23 is a cross-sectional view of the device 2 of FIG. 19 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 23, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

The device 2 of FIG. 24 is, for example, a pig having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

FIG. 25 is a side view of the device 2 of FIG. 24, and FIG. 26 is a rear view of the device 2 of FIG. 24.

FIG. 27 is a perspective view from below of the device 2 of FIG. 24. In this Figure, the receiver 20 is visible and receives a nebulizer 30. FIG. 28 is a cross-sectional view of the device 2 of FIG. 24 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 28, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

The device 2 of FIG. 29 is, for example, a plane having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

FIG. 30 is a side view of the device 2 of FIG. 29, and FIG. 31 is a rear view of the device 2 of FIG. 29.

Figure 29:
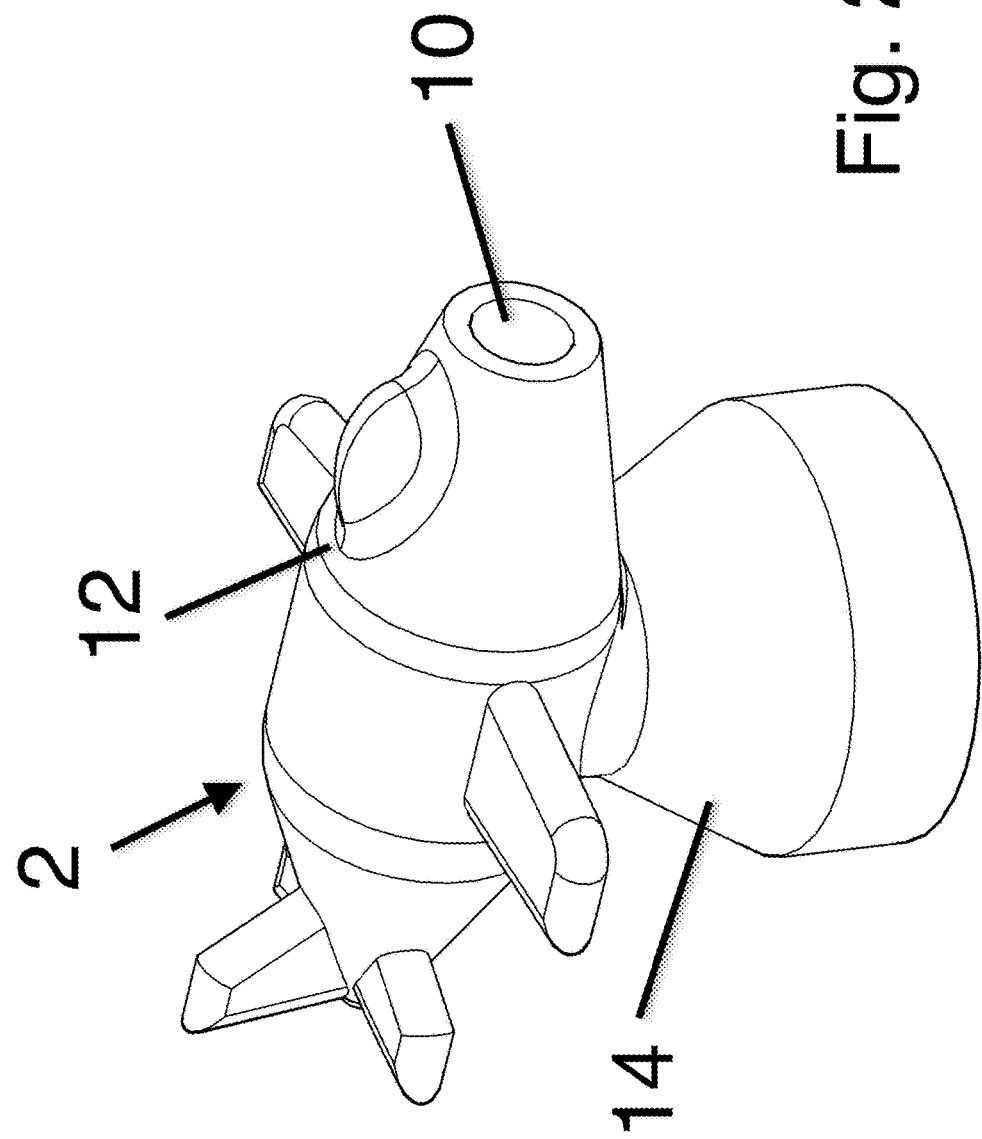
FIG. 29 is an external perspective view of an example directing device for directing nebulized air.
Figure 30:
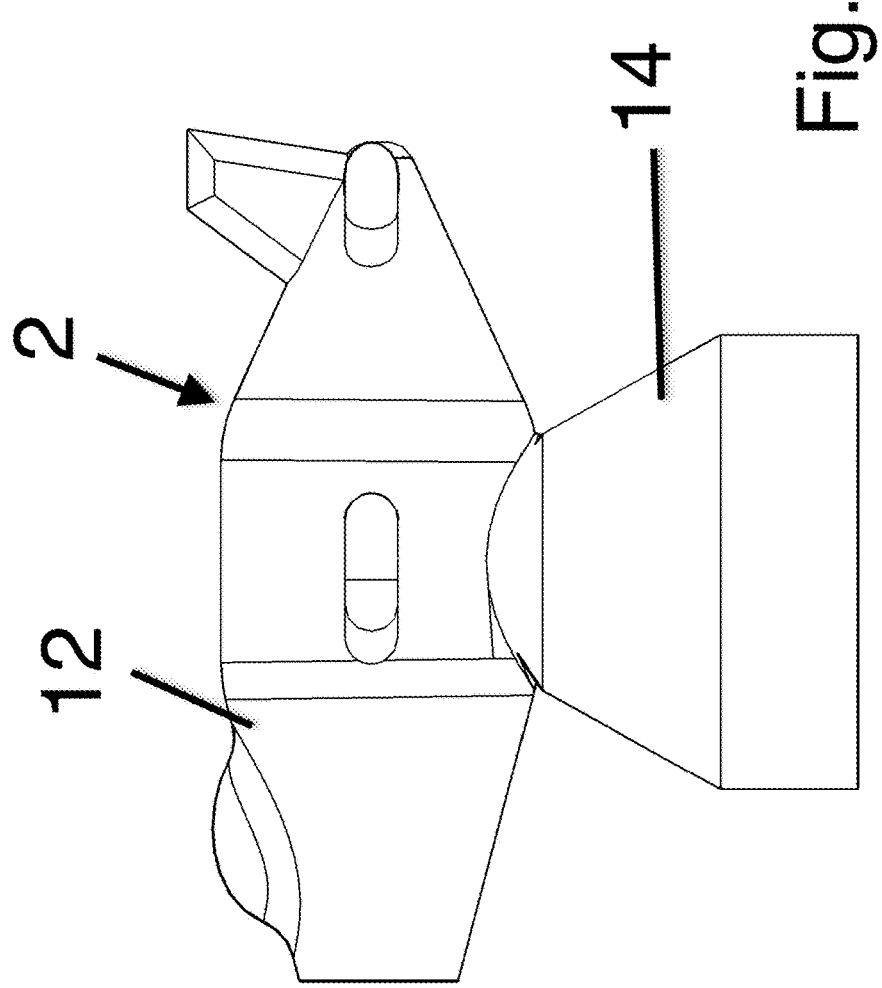
FIG. 30 is a side view of the device of FIG. 29.
Figure 31:
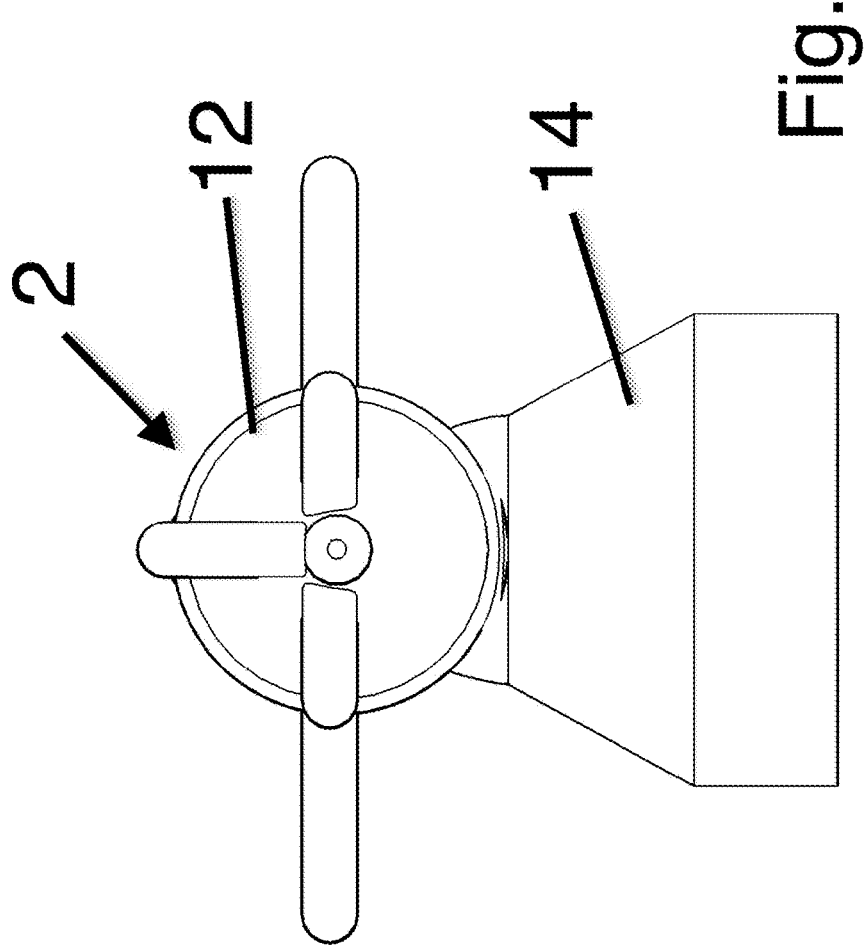
FIG. 31 is a rear view of the device of FIG. 29.

FIG. 32 is a perspective view from below of the device 2 of FIG. 29. In this Figure, the receiver 20 is visible and receives a nebulizer 30. FIG. 33 is a cross-sectional view of the device 2 of FIG. 29 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 33, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

The device 2 of FIG. 34 is, for example, a race car having a head 12 and a body 14. The device 2 includes an exhaust port 10 to expel the nebulized mixture from the directing device. This exhaust port 10 will be proximate or near to or contacting the child or infant in order for the nebulized mixture to be inhaled by the child or infant.

FIG. 35 is a side view of the device 2 of FIG. 34, and FIG. 36 is a rear view of the device 2 of FIG. 34.

FIG. 37 is a perspective view from below of the device 2 of FIG. 34. In this Figure, the receiver 20 is visible and receives a nebulizer 30. FIG. 38 is a cross-sectional view of the device 2 of FIG. 34 showing the interior passages. The receiver 20 includes a circular wall 22 which frictionally holds the nebulizer 30. Preferably, the nebulizer 30 is held in place by the receiver 20 of the directing device 2 by friction, although other mechanical supporting mechanisms may be utilized such as a screw-mechanism, a latch, or a twist-lock system in order to retain the nebulizer within the receiver, for example.

As shown in the cross-sectional view of FIG. 38, the receiver 22 is connected to a passage 24. The exhaust port 10 is connected to a passage 28. The passages 24 and angular passage 26 are connected by a transition 18. Passage 28 is connected to passage 24 and transition 18 by an angular passage 26.

According to an alternative embodiment, the device 2 which directs nebulized vapor includes a protrusion which may be placed in the child's or infant's mouth in order to keep the device proximate to the face or nose of the child or infant.

The directing device 2 may be made of any desired material. According to one embodiment, the device is made of silicone, plastic or rubber. The material that comes in contact with the nebulized mixture preferably does not react with the nebulized mixture. Thus, according to one embodiment, the inner passages and outer body are made of the same material. This makes manufacturing more simple and economical. According to another embodiment, the inner passages and outer body are made of different materials. According to an embodiment, the passages are made of a material, which does not interact with the nebulized mixture and is suitable for use with a nebulizer system, and the outer novelty features of the device are not necessarily required to be made of a different material than the internal passages.

The directing device 2 contains a transition 18 within the device that enables the nebulized mixture to be channeled and directed from the nebulizer into the internal passages 26 and 28 of the directing device 2. This transition 18 enables the device to accelerate the velocity of the nebulized mixture to enable the nebulized mixture to exit the device and travel a further distance to a face or nose of the child or infant. This acceleration occurs because the diameter of the transition 18 is less than the diameter of the angular passage 26 and the passage 28. Additionally, the channels within the directing device 2 enable this velocity to be maintained until it exits the device as the diameter of the passages 26 and/or 28 are constant or substantially constant. Alternatively, the transition to accelerate the nebulized mixture is not limited to being before the angular passage 26, but can be placed after the angular passage, or as part of the angular passage. As long as the transition is of a smaller diameter than an upstream passage, the transition will accelerate the nebulized mixture.

The invention includes the entire system, the directing device, and a method of directing the vapor.

Obviously, numerous modifications and variations of the present invention are possible in light of the above teachings. It is therefore to be understood that within the scope of the appended claims, the invention may be practiced otherwise than as specifically described herein.

The invention claimed is:

1. A device for directing a nebulized mixture, comprising:
   an external shape in the form of a novelty and comprising a body portion and a head portion, the head portion having a face;
   an exhaust port to expel the nebulized mixture from the device directly into the air; and
   a series of internal passages, including:
      a first passage defining a receiving cavity and extending from a base of the body portion to a second passage within the body portion,
      wherein a central axis of the first passage and a central axis of the second passage are vertically aligned, and
      wherein a diameter of the first passage is greater than a diameter of the second passage,
      a third passage extending from the second passage to a fourth passage, the third passage having an angular bend which results in the fourth passage having an angle of at least 45 degrees relative to the first and second passages,
   wherein the fourth passage and the exhaust port are located within the head portion of the device, the exhaust port being positioned on the face of the device.

2. The device according to claim 1, wherein the novelty is one of an animal, a clown, a figurine, and a character.

3. The device according to claim 1, wherein one of the passages comprises:
   a transition with a smaller diameter than an upstream passage within the device to accelerate with the nebulized mixture.

4. The device according to claim 3, wherein one of the passages comprises:
   a section which is a same diameter as an upstream portion of said one of the passages to maintain a velocity of the nebulized mixture.

5. The device according to claim 1, wherein one of the passages comprises:
   a section which is a same diameter as an upstream portion of said one of the passages to maintain a velocity of the nebulized mixture.

6. A method of directing a nebulized mixture comprising:
   receiving the nebulized mixture by a device which has an external shape of a novelty and includes a body portion, a head portion having a face, and a receiving cavity which directly holds a nebulizer;

directing the nebulized mixture which has been received by the device through a series of internal passages within the device; and exhausting into the air towards a face of a person the nebulized mixture which has been directed by the device, wherein the device through which the nebulized mixture passes includes:

an exhaust port to expel the nebulized mixture from the device directly into the air; and the series of internal passages, including:

a first passage defining the receiving cavity and extending from a base of the body portion to a second passage within the body portion, wherein a central axis of the first passage and a central axis of the second passage are vertically aligned, and wherein a diameter of the first passage is greater than a diameter of the second passage, a third passage extending from the second passage to a fourth passage, the third passage having an angular bend which results in the fourth passage having an angle of at least 45 degrees relative to the first and second passages, wherein the fourth passage and the exhaust port are located within the head portion of the device, the exhaust port being positioned on the face of the device.

7. The method according to claim 6, wherein the novelty is one of an animal, a clown, a figurine, and a character.

8. The method according to claim 6, wherein one of the passages comprises:

a transition with a smaller diameter than an upstream passage within the device to accelerate the nebulized mixture.

9. The method according to claim 8, wherein one of the passages comprises:

a section which is a same diameter as an upstream portion of said one of the passages to maintain a velocity of the nebulized mixture that will be expelled directly into the air.

10. The method according to claim 6, wherein one of the passages comprises:

a section which is a same diameter as an upstream portion of said one of the passages to maintain a velocity of the nebulized mixture that will be expelled directly into the air.

* * * * *